United States Patent
Harper et al.

(10) Patent No.: US 8,718,739 B2
(45) Date of Patent: May 6, 2014

(54) ANALYTE SENSOR CALIBRATION MANAGEMENT

(71) Applicant: Abbott Diabetes Care Inc., Alameda, CA (US)

(72) Inventors: Wesley Scott Harper, Alameda, CA (US); Timothy Christian Dunn, San Francisco, CA (US); Erwin Satrya Budiman, Fremont, CA (US); Kenneth J. Doniger, Menlo Park, CA (US); Gary Alan Hayter, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 13/729,075

(22) Filed: Dec. 28, 2012

(65) Prior Publication Data
US 2013/0116527 A1    May 9, 2013

Related U.S. Application Data

(63) Continuation of application No. 12/363,712, filed on Jan. 30, 2009, now Pat. No. 8,346,335.

(60) Provisional application No. 61/040,633, filed on Mar. 28, 2008.

(51) Int. Cl.
*A61B 5/05*    (2006.01)
*A61B 5/00*    (2006.01)

(52) U.S. Cl.
USPC ............ 600/347; 600/309; 600/345; 600/365

(58) Field of Classification Search
USPC .................................. 600/345, 347, 365, 309
See application file for complete search history.

(56) References Cited

U.S. PATENT DOCUMENTS

| 3,581,062 A | 5/1971 | Aston |
| 3,926,760 A | 12/1975 | Allen et al. |
| 3,949,388 A | 4/1976 | Fuller |

(Continued)

FOREIGN PATENT DOCUMENTS

| CA | 2468577 | 6/2003 |
| CA | 2678336 | 5/2008 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Patricia Mallari
*Assistant Examiner* — Christian Jang
(74) *Attorney, Agent, or Firm* — Jackson & Co., LLP

(57) ABSTRACT

Methods and devices to detect analyte in body fluid are provided. Embodiments include positioning an analyte sensor in fluid contact with an analyte, detecting an attenuation in a signal from an analyte sensor after positioning during a predetermined time period, categorizing the detected attenuation in the analyte sensor signal based, at least in part, on one or more characteristics of the signal, performing signal processing to generate a reportable data associated with the detected analyte sensor signal during the predetermined time period, managing if and when to request additional reference signal measurements, and managing if and when to temporarily not display results.

20 Claims, 8 Drawing Sheets

(56) References Cited

U.S. PATENT DOCUMENTS

| | | |
|---|---|---|
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,202,261 A | 4/1993 | Musho et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,328,460 A | 7/1994 | Lord et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,733,259 A | 3/1998 | Valcke et al. |
| 5,772,586 A | 6/1998 | Heinonen et al. |
| 5,791,344 A | 8/1998 | Schulman et al. |
| 5,899,855 A | 5/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,046 B1 | 11/2002 | Say et al. |
| 6,514,718 B2 | 2/2003 | Heller et al. |
| 6,544,212 B2 | 4/2003 | Galley et al. |
| 6,546,268 B1 | 4/2003 | Ishikawa et al. |
| 6,551,494 B1 | 4/2003 | Heller et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |

(56) References Cited

U.S. PATENT DOCUMENTS

| | | |
|---|---|---|
| 6,565,509 B1 | 5/2003 | Say et al. |
| 6,571,128 B2 | 5/2003 | Lebel et al. |
| 6,572,545 B2 | 6/2003 | Knobbe et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Bocko et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,950,708 B2 | 9/2005 | Bowman IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,022,072 B2 | 4/2006 | Fox et al. |
| 7,024,245 B2 | 4/2006 | Lebel et al. |
| 7,025,425 B2 | 4/2006 | Kovatchev et al. |
| 7,029,444 B2 | 4/2006 | Shin et al. |
| 7,041,068 B2 | 5/2006 | Freeman et al. |
| 7,043,287 B1 | 5/2006 | Khalil et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,134,999 B2 | 11/2006 | Brauker et al. |
| 7,136,689 B2 | 11/2006 | Shults et al. |
| 7,153,265 B2 | 12/2006 | Vachon |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,241,266 B2 | 7/2007 | Zhou et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,401,111 B1 | 7/2008 | Batman et al. |
| 7,402,153 B2 | 7/2008 | Steil et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,774,145 B2 | 8/2010 | Brauker et al. |
| 7,778,680 B2 | 8/2010 | Goode, Jr. et al. |
| 7,826,981 B2 | 11/2010 | Goode et al. |
| 7,885,698 B2 | 2/2011 | Feldman et al. |
| 7,899,511 B2 | 3/2011 | Shults et al. |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,928,850 B2 | 4/2011 | Hayter et al. |
| 7,974,672 B2 | 7/2011 | Shults et al. |
| 7,976,467 B2 | 7/2011 | Young et al. |
| 8,010,174 B2 | 8/2011 | Goode et al. |
| 8,066,639 B2 | 11/2011 | Nelson et al. |
| 8,216,138 B1 | 7/2012 | McGarraugh et al. |
| 2002/0019022 A1 | 2/2002 | Dunn et al. |
| 2002/0042090 A1 | 4/2002 | Heller et al. |
| 2002/0068860 A1 | 6/2002 | Clark |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0161288 A1 | 10/2002 | Shin et al. |

(56) References Cited

U.S. PATENT DOCUMENTS

| | | |
|---|---|---|
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0254433 A1 | 12/2004 | Bandis et al. |
| 2004/0267300 A1 | 12/2004 | Mace |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0287620 A1 | 12/2005 | Heller et al. |
| 2006/0001538 A1 | 1/2006 | Kraft et al. |
| 2006/0004270 A1 | 1/2006 | Bedard et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0091006 A1 | 5/2006 | Wang et al. |
| 2006/0142651 A1* | 6/2006 | Brister et al. .................. 600/347 |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0222566 A1 | 10/2006 | Brauker et al. |
| 2006/0224109 A1 | 10/2006 | Steil et al. |
| 2006/0229512 A1 | 10/2006 | Petisce et al. |
| 2006/0247508 A1 | 11/2006 | Fennell |
| 2006/0253296 A1 | 11/2006 | Liisberg et al. |
| 2006/0264785 A1 | 11/2006 | Dring et al. |
| 2006/0272652 A1 | 12/2006 | Stocker et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0038053 A1 | 2/2007 | Berner et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078314 A1 | 4/2007 | Grounsell et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0093786 A1 | 4/2007 | Goldsmith et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0197889 A1 | 8/2007 | Brauker et al. |

(56) References Cited

U.S. PATENT DOCUMENTS

| | | |
|---|---|---|
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0232880 A1 | 10/2007 | Siddiqui et al. |
| 2007/0235331 A1 | 10/2007 | Simpson et al. |
| 2007/0249922 A1 | 10/2007 | Peyser et al. |
| 2007/0270672 A1 | 11/2007 | Hayter |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234992 A1 | 9/2008 | Ray et al. |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0278331 A1 | 11/2008 | Hayter et al. |
| 2008/0287755 A1 | 11/2008 | Sass et al. |
| 2008/0287761 A1 | 11/2008 | Hayter |
| 2008/0287762 A1 | 11/2008 | Hayter et al. |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev |
| 2008/0319279 A1 | 12/2008 | Ramsay et al. |
| 2009/0005665 A1 | 1/2009 | Hayter et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054750 A1 | 2/2009 | Jennewine |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0099436 A1 | 4/2009 | Brister et al. |
| 2009/0105570 A1 | 4/2009 | Sloan et al. |
| 2009/0105636 A1 | 4/2009 | Hayter et al. |
| 2009/0112154 A1 | 4/2009 | Montgomery et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0157430 A1 | 6/2009 | Rule et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0210249 A1 | 8/2009 | Rasch-Menges et al. |
| 2009/0216103 A1 | 8/2009 | Brister et al. |

(56) References Cited

U.S. PATENT DOCUMENTS

| | | |
|---|---|---|
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0023291 A1 | 1/2010 | Hayter et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0152548 A1 | 6/2010 | Koski |
| 2010/0152554 A1 | 6/2010 | Steine et al. |
| 2010/0160757 A1 | 6/2010 | Weinert et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode, Jr. et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185070 A1 | 7/2010 | Brister et al. |
| 2010/0185071 A1 | 7/2010 | Simpson et al. |
| 2010/0185072 A1 | 7/2010 | Goode, Jr. et al. |
| 2010/0185075 A1 | 7/2010 | Brister et al. |
| 2010/0191082 A1 | 7/2010 | Brister et al. |
| 2010/0191087 A1 | 7/2010 | Talbot et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0204557 A1 | 8/2010 | Kiaie et al. |
| 2010/0212583 A1 | 8/2010 | Brister et al. |
| 2010/0214104 A1 | 8/2010 | Goode, Jr. et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0234710 A1 | 9/2010 | Budiman et al. |
| 2010/0240975 A1 | 9/2010 | Goode, Jr. et al. |
| 2010/0240976 A1 | 9/2010 | Goode et al. |
| 2010/0259543 A1 | 10/2010 | Tarassenko et al. |
| 2010/0261987 A1 | 10/2010 | Kamath et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324403 A1 | 12/2010 | Brister et al. |
| 2010/0331644 A1 | 12/2010 | Neale et al. |
| 2010/0331648 A1 | 12/2010 | Kamath et al. |
| 2010/0331651 A1 | 12/2010 | Groll |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0046467 A1 | 2/2011 | Simpson et al. |
| 2011/0077469 A1 | 3/2011 | Blocker et al. |
| 2011/0077490 A1 | 3/2011 | Simpson et al. |
| 2011/0118579 A1 | 5/2011 | Goode, Jr. et al. |
| 2011/0118580 A1 | 5/2011 | Goode, Jr. et al. |
| 2011/0123971 A1 | 5/2011 | Berkowitz et al. |
| 2011/0124992 A1 | 5/2011 | Brauker et al. |
| 2011/0124997 A1 | 5/2011 | Goode, Jr. et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0178378 A1 | 7/2011 | Brister et al. |
| 2011/0184752 A1 | 7/2011 | Ray et al. |
| 2011/0190614 A1 | 8/2011 | Brister et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0218414 A1 | 9/2011 | Kamath et al. |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0290645 A1 | 12/2011 | Brister et al. |
| 2011/0313543 A1 | 12/2011 | Brauker et al. |
| 2011/0319739 A1 | 12/2011 | Kamath et al. |
| 2011/0320130 A1 | 12/2011 | Valdes et al. |
| 2012/0035445 A1 | 2/2012 | Boock et al. |
| 2012/0040101 A1 | 2/2012 | Tapsak et al. |

(56) References Cited

U.S. PATENT DOCUMENTS

| | | |
|---|---|---|
| 2012/0046534 A1 | 2/2012 | Simpson et al. |
| 2012/0078071 A1 | 3/2012 | Bohm et al. |
| 2012/0108934 A1 | 5/2012 | Valdes et al. |

FOREIGN PATENT DOCUMENTS

| | | |
|---|---|---|
| CA | 2626349 | 9/2008 |
| CA | 2728831 | 7/2011 |
| CA | 2617965 | 10/2011 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 2031534 | 3/2009 |
| EP | 1725163 | 12/2010 |
| WO | WO-96/25089 | 8/1996 |
| WO | WO-96/35370 | 11/1996 |
| WO | WO-99/27849 | 12/1997 |
| WO | WO-98/35053 | 8/1998 |
| WO | WO-99/28736 | 12/1998 |
| WO | WO-99/56613 | 11/1999 |
| WO | WO-00/49940 | 8/2000 |
| WO | WO-00/59370 | 10/2000 |
| WO | WO-00/74753 | 12/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/057027 | 7/2003 |
| WO | WO-03/076893 | 9/2003 |
| WO | WO-03/082091 | 10/2003 |
| WO | WO-03/085372 | 10/2003 |
| WO | WO-2004/060455 | 7/2004 |
| WO | WO-2004/061420 | 7/2004 |
| WO | WO-2005/041766 | 5/2005 |
| WO | WO-2005/057175 | 6/2005 |
| WO | WO-2005/065538 | 7/2005 |
| WO | WO-2005/065542 | 7/2005 |
| WO | WO-2005/089103 | 9/2005 |
| WO | WO-2006/020212 | 2/2006 |
| WO | WO-2006/024671 | 3/2006 |
| WO | WO-2006/072035 | 7/2006 |
| WO | WO-2006/079114 | 7/2006 |
| WO | WO-2006/118947 | 11/2006 |
| WO | WO-2007/016399 | 2/2007 |
| WO | WO-2007/019289 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/021913 | 2/2008 |
| WO | WO-2008/042760 | 4/2008 |
| WO | WO-2008/048452 | 4/2008 |
| WO | WO-2008/052374 | 5/2008 |
| WO | WO-2008/062099 | 5/2008 |
| WO | WO-2008/086541 | 7/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2008/144445 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |
| WO | WO-2010/062898 | 6/2010 |
| WO | WO-2011/000528 | 1/2011 |
| WO | WO-2011/104616 | 9/2011 |

OTHER PUBLICATIONS

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results from a Non-Invasive Blood Glucose Monitor", *Optical Diagnostic and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56 No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabates Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

(56) References Cited

OTHER PUBLICATIONS

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics with 0.3-mm Amperometric E161. of Glucose Delivery to Subcutaneous Tissue in Rats Measured Microsensors", *the American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "*Diabetes mellitus*: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

Chinese Patent Application No. 200980119054.7, Original Language and English Translation of Office Action mailed Dec. 21, 2012.

Chinese Patent Application No. 200980119054.7, Original Language and English Translation of Office Action mailed Jan. 18, 2012.

PCT Application No. PCT/US2009/038698, International Preliminary Report on Patentability mailed Oct. 7, 2010.

PCT Application No. PCT/US2009/038698, International Search Report and Written Opinion of the International Searching Authority mailed Aug. 31, 2009.

U.S. Appl. No. 12/363,712, Notice of Allowance mailed Sep. 28, 2012.

U.S. Appl. No. 12/363,712, Office Action mailed Feb. 1, 2012.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Chinese Patent Application No. 200980119054.7, Original Language and English Translation of Office Action mailed Jul. 10, 2013.

European Patent Application No. 09726272.9, Extended European Search Report mailed Apr. 4, 2013.

\* cited by examiner

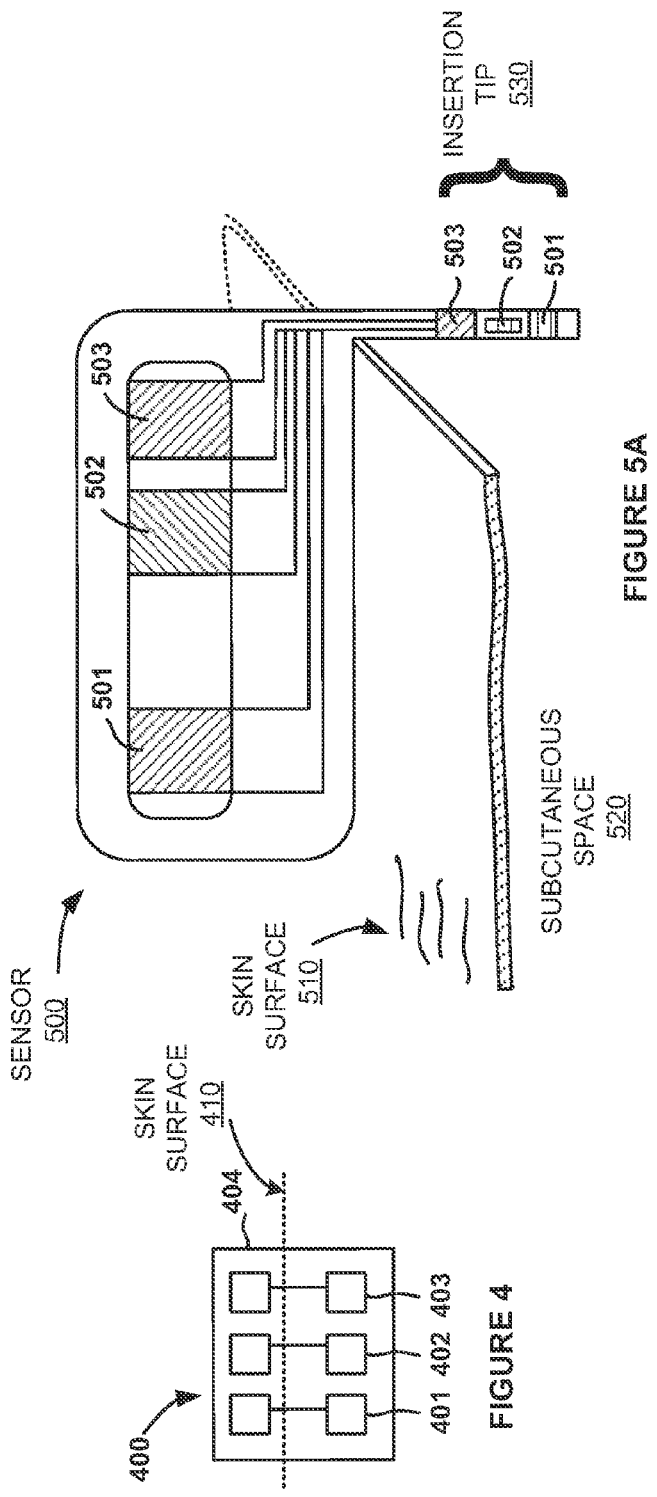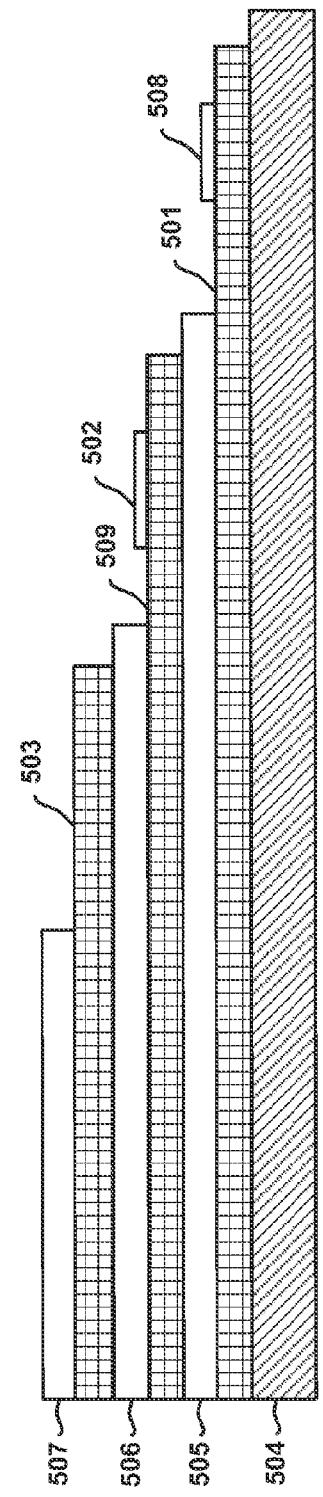

ANALYTE SENSOR CALIBRATION MANAGEMENT

RELATED APPLICATIONS

The present application is a continuation of U.S. patent application Ser. No. 12/363,712 filed Jan. 30, 2009, now U.S. Pat. No. 8,346,335, which claims priority under 35 U.S.C. §119(e) to U.S. provisional application No. 61/040,633 filed Mar. 28, 2008 entitled "Analyte Sensor Calibration Management," and assigned to the assignee of the present application, Abbott Diabetes Care Inc. of Alameda, Calif., the disclosures of each of which are incorporated herein by reference for all purposes.

BACKGROUND

The detection of the level of glucose or other analytes, such as lactate, oxygen or the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for continuous or automatic monitoring of analytes, such as glucose, in bodily fluid such as in the blood stream or in interstitial fluid. Some of these analyte measuring devices are configured so that at least a portion of the devices are positioned below a skin surface of a user, e.g., in a blood vessel or in the subcutaneous tissue of a user.

Following the sensor insertion, the resulting potential trauma to the skin and/or underlying tissue, for example, by the sensor introducer and/or the sensor itself, may, at times, result in instability of signals monitored by the sensor. This may occur in a number of analyte sensors, but not in all cases. This instability is characterized by a decrease in the sensor signal, and when this occurs, generally, the analyte levels monitored may not be reported, recorded or output to the user.

Proper calibration of an analyte sensor with a reference glucose measurement or reading is important for accurate sensor performance. Calibration is a process by which a conversion factor (or sensitivity) is determined and represented, in its simplest form, as a ratio of the electrical current generated by the analyte sensor to the reference blood glucose value (for example, from an in vitro blood glucose meter) associated in time (for example, relatively time corresponding) with the current signal from the analyte sensor. Ideally, the sensitivity is constant throughout the life of the analyte sensor when positioned in fluid contact with an analyte of a user (such as interstitial fluid). In practice, however, the sensitivity may vary over time. It has been observed that a depression or attenuation in the sensitivity, usually following a predetermined time period measured from the insertion or positioning of the analyte sensor, occurs sometimes for up to 24 hours for some analyte sensors. This signal characteristic is referred to as Early Sensitivity Attenuation (ESA) or referred to as ESA condition. The ESA condition may be a result of a physiological response to the introduction of the analyte sensor to the subcutaneous tissue, and may be present for any subcutaneously inserted analyte sensor.

Generally, the use of a standard calibration sensitivity calculation does not address the signal attenuation. A typical standard calibration does not detect or manage the attenuated signal characteristics, and also may potentially update or modify the calibration sensitivity using the erroneous and attenuated sensor signal. When sensor calibration is performed while the sensor is undergoing a signal attenuation event, the reported or resulting sensor data may be erroneously high when the sensor sensitivity has recovered after the termination of the signal attenuation event. Such high biased results may be clinically unsafe, as they may lead to missed hypoglycaemic events, or overdoses of medication such as insulin. On the other hand, when sensor calibration is performed prior to an early signal attenuation event, erroneously low biased sensor data will likely result during the period of the sensor sensitivity depression. Such low glucose results may, depending on the magnitude of the early signal attenuation event, result in false hypoglycaemia alarms or missed hyperglycaemic events.

Another approach has been to delay the sensor calibration until after the early signal attenuation period measured, for example, from the initial sensor insertion in the patient. However, this approach prevents the reporting of the potentially erroneous analyte level monitored from the sensor during this period, but results in low data yield due to the undesirable delay for the display or reporting of the monitored analyte levels from the sensors regardless of whether or not early signal attenuation is present.

SUMMARY

Embodiments of the subject disclosure include device and methods of detecting a change, e.g., a decrease (or monitoring for a change in the signal level), in sensitivity associated with an analyte sensor to identify or detect early signal attenuation (ESA). The detected or monitored analyte level is reported or output after a short sensor equilibration time period (e.g., approximately one hour or more or less) when detected change is not associated with early signal attenuation.

Also provided are systems, computer program products, and kits.

BRIEF DESCRIPTION OF THE DRAWINGS

FIG. 4 shows a schematic diagram of an embodiment of an analyte sensor according to the present disclosure;

FIGS. 5A-5B show a perspective view and a cross sectional view, respectively of an embodiment the analyte sensor of FIG. 4;

DETAILED DESCRIPTION

Figure 1:
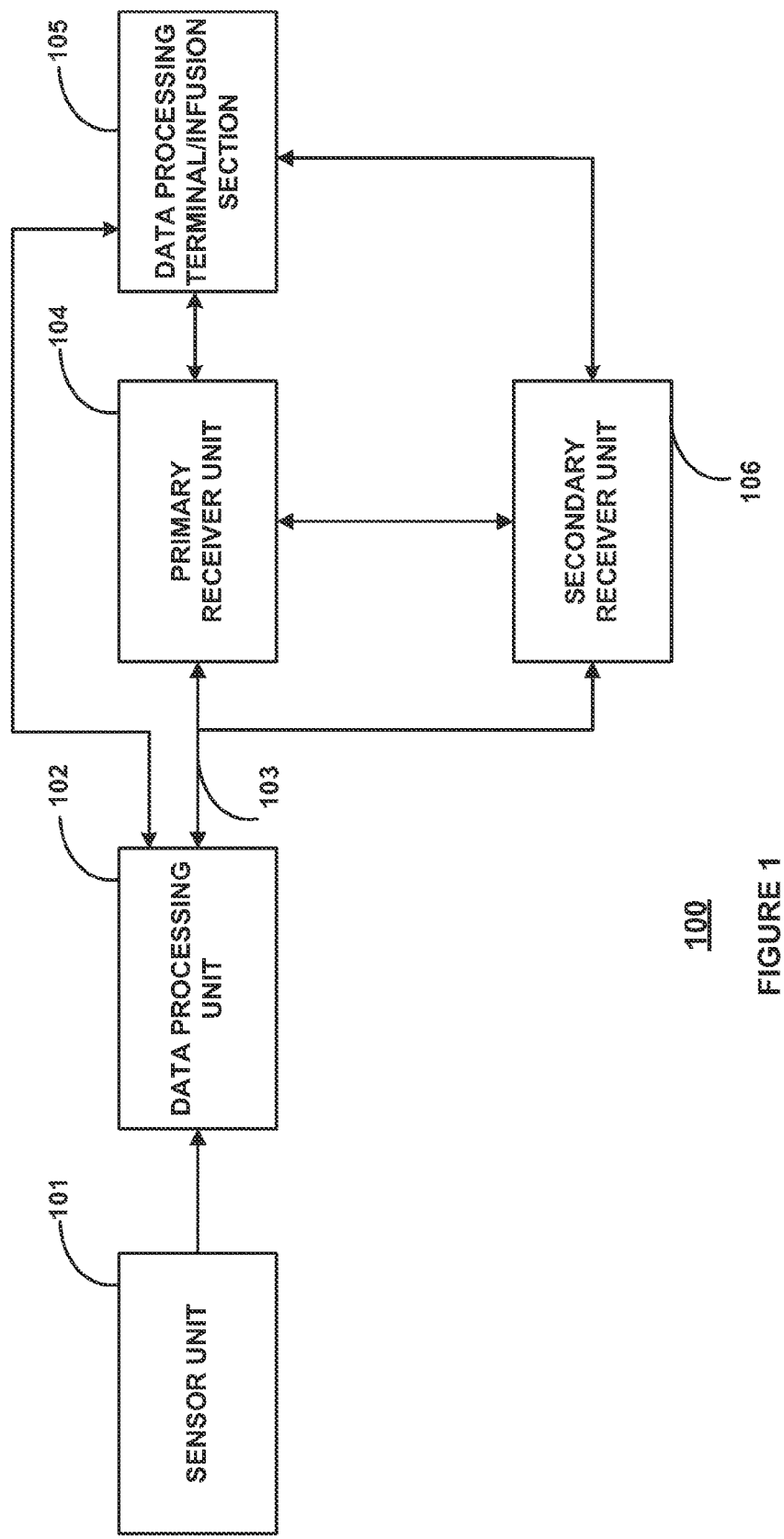
FIG. 1 shows a block diagram of an embodiment of a data monitoring and management system according to the present disclosure.

Within the scope of the present disclosure, early signal attenuation (ESA) condition which may be attributable to associated instability of monitored analyte levels resulting from skin and/or tissue trauma when the sensor is transcutaneously positioned under the skin layer of a user. Analyte sensors may be manufactured and/or the trauma resulting from the inserted sensor may be such that the sensor attains a stability point or an equilibration level after a relatively short time period—for example, within approximately one hour (or less) from the initial sensor insertion.

In one aspect, the signals from the analyte sensor may be monitored for ESA condition detection. When no ESA condition is detected and/or the sensor reaches the equilibration level within the short time period, then the analyte monitoring system may be configured to request a reference blood glucose value from the user, for example, a fingerstick in vitro test using a blood glucose meter, to calibrate the sensor signals, and thereafter, report or display to the user the monitored analyte levels. In this manner, in one aspect, the initial baseline calibration of the analyte sensor may be performed after approximately one hour from the initial sensor insertion, and upon successful calibration, the resulting real time analyte levels displayed to the user, or otherwise stored or logged in the analyte monitoring system and/or transmitted to a remote device or terminal.

When the potential for ESA condition or actual ESA condition is detected after the initial equilibration time period, for example, of approximately one hour from the sensor insertion, the analyte monitoring system may be configured to alert the user to wait a predetermined time period before providing the reference blood glucose value to provide the sensor to stabilize, or alternatively, the user may be prompted to provide the reference blood glucose value to confirm whether the potential ESA condition monitored is an actual occurrence of ESA condition.

In one aspect, the scheduled calibration of the analyte sensor may be delayed to provide the sensor with an additional time period to reach a desired or acceptable stability level. Among other conditions, boundaries may be established to provide the sensor with an additional time period to reach a predetermined or acceptable stability level before the received analyte sensor signals are calibrated, and thus, provided to the user. Within the scope of the present disclosure, other conditions and parameters may be provided to establish or detect ESA condition during a predetermined time period from the initial sensor insertion, for example, during the first 24 hours of sensor insertion.

In this manner, in one aspect, when it is determined that the transcutaneously positioned sensor has reached an acceptable stability level resulting in the desired or predetermined equilibration level, the analyte monitoring system may display or otherwise accept, output, log, or process the monitored analyte level, substantially in real time, received from the transcutaneously positioned sensor. In one aspect, the acceptable stability level is analyzed at approximately one hour from the initial sensor insertion, and thereafter, if no ESA condition is detected, the analyte sensor data is calibrated against a reference blood glucose value (for example, received from an in vitro glucose meter).

In the case where ESA condition or the potential for such signal attenuation is detected, the analyte monitoring system may be configured in one embodiment to perform one or more routines or functions to verify the sensor related signals to confirm the ESA condition, to notify the user to refrain from performing a fingerstick test using a blood glucose meter to provide a reference blood glucose value for calibration, among others.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and devices for detecting at least one analyte such as glucose in body fluid. In certain embodiments, the present disclosure relates to the continuous and/or automatic in vivo monitoring of the level of an analyte using an analyte sensor.

Accordingly, embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise. The analyte level may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the subject disclosure may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days or more, e.g., about three days or more, e.g., about five days or more, e.g., about seven days or more, e.g., about several weeks or at least one month. Future analyte levels may be predicted based on information obtained, e.g., the current analyte level at time t0, the rate of change of the analyte, etc. Predictive alarms may notify the user of predicted analyte levels that may be of concern prior to or in advance of the analyte level reaching the future level. This enables the user an opportunity to take corrective action.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104, the data processing terminal 105 or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or bi-directional communication device.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In one aspect, the primary receiver unit 104 may include an analog interface section including an RF receiver and an antenna that is configured to communicate with the data processing unit 102 via the communication link 103, data processing unit 102 and a data processing section for processing the received data from the data processing unit 102 such as data decoding, error detection and correction, data clock generation, and/or data bit recovery.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone or similar phone), mp3 player, pager, and the like), drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In particular embodiments, the data processing terminal 105, which may include an insulin pump, may be configured to receive the analyte signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1 may use one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
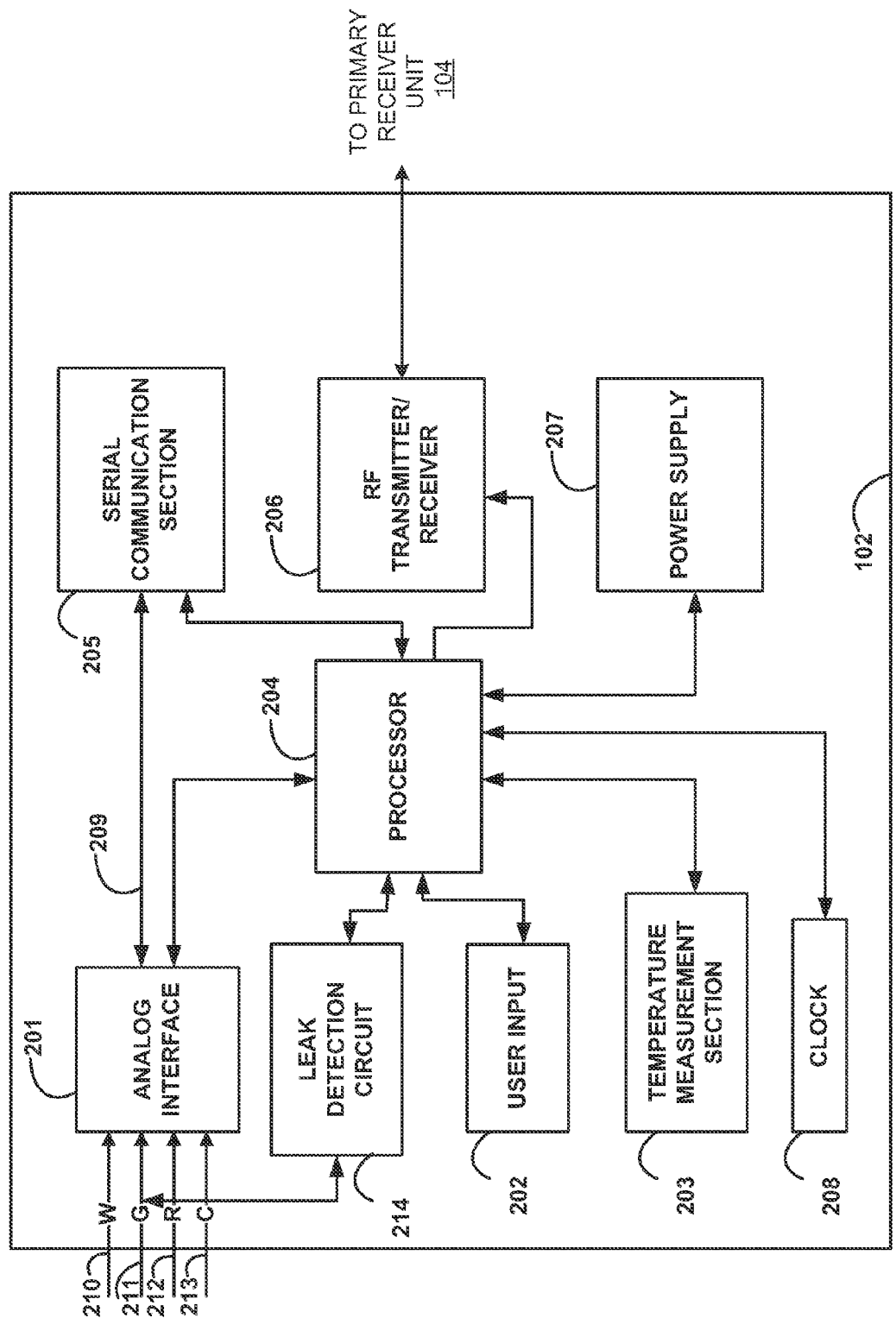
FIG. 2 shows a block diagram of an embodiment of the transmitter unit of the data monitoring and management system of FIG. 1.

FIG. 2 is a block diagram of the data processing unit of the data monitoring and detection system shown in FIG. 1 in accordance with certain embodiments. The data processing unit 102 thus may include one or more of an analog interface 201 configured to communicate with the sensor 101 (FIG. 1), a user input 202, and a temperature detection section 203, each of which is operatively coupled to a transmitter processor 204 such as a central processing unit (CPU). The transmitter may include user input and/or interface components or may be free of user input and/or interface components.

Further shown in FIG. 2 are serial communication section 205 and an RF transmitter 206, each of which is also operatively coupled to the transmitter processor 204. Moreover, a power supply 207, such as a battery, may also be provided in the data processing unit 102 to provide the necessary power for the data processing unit 102. Additionally, as can be seen from the Figure, clock 208 may be provided to, among others, supply real time information to the transmitter processor 204.

As can be seen in the embodiment of FIG. 2, the sensor unit 101 (FIG. 1) includes four contacts, three of which are electrodes—work electrode (W) 210, guard contact (G) 211, reference electrode (R) 212, and counter electrode (C) 213, each operatively coupled to the analog interface 201 of the data processing unit 102. In certain embodiments, each of the work electrode (W) 210, guard contact (G) 211, reference electrode (R) 212, and counter electrode (C) 213 may be made using a conductive material that may be applied by, e.g., chemical vapor deposition (CVD), physical vapor deposition, sputtering, reactive sputtering, printing, coating, ablating (e.g., laser ablation), painting, dip coating, etching, and the like. Materials include, but are not limited to, aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The processor 204 may be configured to generate and/or process control signals to the various sections of the data processing unit 102 during the operation of the data processing unit 102. In certain embodiments, the processor 204 also includes memory (not shown) for storing data such as the identification information for the data processing unit 102, as well as the data associated with signals received from the sensor 101. The stored information may be retrieved and processed for transmission to the primary receiver unit 104 under the control of the processor 204. Furthermore, the power supply 207 may include a commercially available battery.

In certain embodiments, a manufacturing process of the data processing unit 102 may place the data processing unit 102 in the lower power, non-operating state (i.e., post-manufacture sleep mode). In this manner, the shelf life of the data processing unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the data processing unit 102 shown in FIG. 2.

Referring back to FIG. 2, the power supply section 207 of the data processing unit 102 in one embodiment may include a rechargeable battery unit that may be recharged by a separate power supply recharging unit (for example, provided in the receiver unit 104) so that the data processing unit 102 may be powered for a longer period of usage time. In certain embodiments, the data processing unit 102 may be configured without a battery in the power supply section 207, in which case the data processing unit 102 may be configured to receive power from an external power supply source (for example, a battery, electrical outlet, etc.) as discussed in further detail below.

Referring yet again to FIG. 2, a temperature detection section 203 of the data processing unit 102 is configured to monitor the temperature of the skin near the sensor insertion site. The temperature reading may be used to adjust the analyte readings obtained from the analog interface 201. Also shown is a leak detection circuit 214 coupled to the guard trace (G) 211 and the processor 204 in the data processing unit 102 of the data monitoring and management system 100. The leak detection circuit 214 may be configured to detect leakage current in the sensor 101 to determine whether the measured sensor data are corrupt or whether the measured data from the sensor 101 is accurate. Such detection may trigger a notification to the user.

Figure 3:
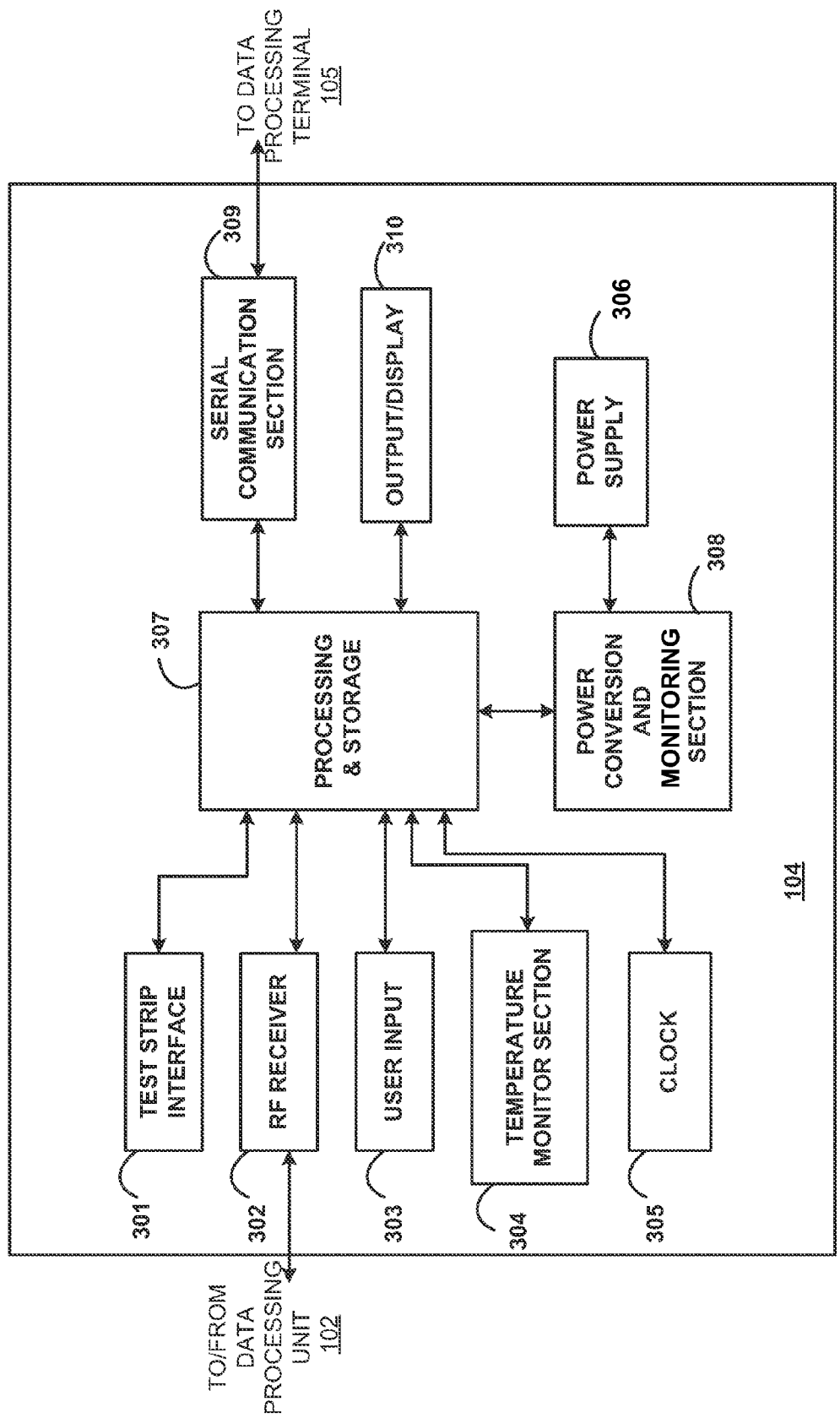
FIG. 3 shows a block diagram of an embodiment of the receiver/monitor unit of the data monitoring and management system of FIG. 1.

FIG. 3 is a block diagram of the receiver/monitor unit such as the primary receiver unit 104 of the data monitoring and management system shown in FIG. 1 in accordance with certain embodiments. The primary receiver unit 104 includes one or more of: a blood glucose test strip interface 301, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In certain embodiments, the test strip interface 301 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 310 of the primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® blood glucose test strips from Abbott Diabetes Care Inc. Glucose information obtained by the in vitro glucose testing device may be used for a variety of purposes, computations, etc. For example, the information may be used to calibrate sensor 101, confirm results of the sensor 101 to increase the confidence thereof (e.g., in instances in which information obtained by sensor 101 is employed in therapy related decisions), etc.

In one aspect, the RF receiver 302 is configured to communicate, via the communication link 103 (FIG. 1) with the RF transmitter 206 of the data processing unit 102, to receive encoded data from the data processing unit 102 for, among others, signal mixing, demodulation, and other data processing. The input 303 of the primary receiver unit 104 is configured to allow the user to enter information into the primary receiver unit 104 as needed. In one aspect, the input 303 may include keys of a keypad, a touch-sensitive screen, and/or a voice-activated input command unit, and the like. The temperature monitor section 304 may be configured to provide temperature information of the primary receiver unit 104 to the processing and storage section 307, while the clock 305 provides, among others, real time or clock information to the processing and storage section 307.

Each of the various components of the primary receiver unit 104 shown in FIG. 3 is powered by the power supply 306 (or other power supply) which, in certain embodiments, includes a battery. Furthermore, the power conversion and monitoring section 308 is configured to monitor the power usage by the various components in the primary receiver unit 104 for effective power management and may alert the user, for example, in the event of power usage which renders the primary receiver unit 104 in sub-optimal operating conditions. The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable (such as USB or serial cable), infrared (IR) or RF link. The output/display 310 of the primary receiver unit 104 is configured to provide, among others, a graphical user interface (GUI), and may include a liquid crystal display (LCD) for displaying information. Additionally, the output/display 310 may also include an integrated speaker for outputting audible signals as well as to provide vibration output as commonly found in handheld electronic devices, such as mobile telephones, pagers, etc. In certain embodiments, the primary receiver unit 104 also includes an electro-luminescent lamp configured to provide backlighting to the output 310 for output visual display in dark ambient surroundings.

Referring back to FIG. 3, the primary receiver unit 104 may also include a storage section such as a programmable, non-volatile memory device as part of the processor 307, or provided separately in the primary receiver unit 104, operatively coupled to the processor 307. The processor 307 may be configured to perform Manchester decoding (or other protocol(s)) as well as error detection and correction upon the encoded data received from the data processing unit 102 via the communication link 103.

In further embodiments, the data processing unit 102 and/or the primary receiver unit 104 and/or the secondary receiver unit 106, and/or the data processing terminal/infusion section 105 may be configured to receive the blood glucose value wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 106, or the data processing terminal/infusion section 105.

Additional detailed descriptions of embodiments of the continuous analyte monitoring system, embodiments of its various components are provided in U.S. Pat. No. 6,175,752 issued Jan. 16, 2001 entitled "Analyte Monitoring Device and Methods of Use", and in application Ser. No. 10/745,878 filed Dec. 26, 2003, issued as U.S. Pat. No. 7,811,231, entitled "Continuous Glucose Monitoring System and Methods of Use", each assigned to the Assignee of the present application.

FIG. 4 schematically shows an embodiment of an analyte sensor in accordance with the present disclosure. The sensor 400 includes electrodes 401, 402 and 403 on a base 404. The sensor may be wholly implantable in a user or may be configured so that only a portion is positioned within (internal) a user and another portion outside (external) a user. For example, the sensor 400 may include a portion positionable above a surface of the skin 410, and a portion positioned below the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 5A shows a perspective view of an embodiment of an electrochemical analyte sensor 500 having a first portion (which in this embodiment may be characterized as a major portion) positionable above a surface of the skin 510, and a second portion (which in this embodiment may be characterized as a minor portion) that includes an insertion tip 530 positionable below the skin, e.g., penetrating through the skin and into, e.g., the subcutaneous space 520, in contact with the user's biofluid such as interstitial fluid. Contact portions of a working electrode 501, a reference electrode 502, and a counter electrode 503 are positioned on the portion of the sensor 500 situated above the skin surface 510. Working electrode 501, a reference electrode 502, and a counter electrode 503 are shown at the second section and particularly at the insertion tip 530. Traces may be provided from the electrode at the tip to the contact, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 501, 502 and 503, of the sensor 500 as well as the substrate and the dielectric layers are provided in a layered configuration or construction. For example, as shown in FIG. 5B, in one aspect, the sensor 500 (such as the sensor unit 101 FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing layer 508.

Referring back to FIG. 5B, a first insulation layer such as a first dielectric layer 505 is disposed or layered on at least a portion of the first conducting layer 501, and further, a second conducting layer 509 may be disposed or stacked on top of at least a portion of the first insulation layer (or dielectric layer) 505. As shown in FIG. 5B, the second conducting layer 509 may provide the reference electrode 502, and in one aspect, may include a layer of silver/silver chloride (Ag/AgCl), gold, etc.

Referring still again to FIG. 5B, a second insulation layer 506 such as a dielectric layer in one embodiment may be disposed or layered on at least a portion of the second conducting layer 509. Further, a third conducting layer 503 may provide the counter electrode 503. It may be disposed on at least a portion of the second insulation layer 506. Finally, a third insulation layer 507 may be disposed or layered on at least a portion of the third conducting layer 503. In this manner, the sensor 500 may be layered such that at least a portion of each of the conducting layers is separated by a respective insulation layer (for example, a dielectric layer).

The embodiment of FIGS. 5A and 5B show the layers having different lengths. Some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing there between and/or include dielectric material or insulation material disposed between the conducting layers/electrodes. Furthermore, in certain embodiments one or more of the electrodes 501, 502, 503 may be disposed on opposing sides of the substrate 504. In such embodiments, contact pads may be on the same or different sides of the substrate. For example, an electrode may be on a first side and its respective contact may be on a second side, e.g., a trace connecting the electrode and the contact may traverse through the substrate.

In certain embodiments, the data processing unit 102 may be configured to perform sensor insertion detection and data quality analysis, information pertaining to which may also be transmitted to the primary receiver unit 104 periodically at the predetermined time interval. In turn, the primary receiver unit 104 may be configured to perform, for example, skin temperature compensation/correction as well as calibration of the sensor data received from the data processing unit 102.

As noted above, analyte sensors may include an analyte-responsive enzyme in a sensing layer. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for analytes, such as oxygen, that can be directly electrooxidized or electroreduced on the working electrode. For these analytes, each working electrode includes a sensing layer (see for example sensing layer 508 of FIG. 5B) formed proximate to or on a surface of a working electrode. In many embodiments, a sensing layer is formed near or on only a small portion of at least a working electrode.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes, e.g., over the counter electrode and/or reference electrode (or counter/reference is provided). The sensing layer may be integral with the material of an electrode.

A sensing layer that is in direct contact with the working electrode may contain an electron transfer agent to transfer electrons directly or indirectly between the analyte and the working electrode, and/or a catalyst to facilitate a reaction of the analyte.

A sensing layer that is not in direct contact with the working electrode may include a catalyst that facilitates a reaction of the analyte. However, such sensing layers may not include an electron transfer agent that transfers electrons directly from the working electrode to the analyte, as the sensing layer is spaced apart from the working electrode. One example of this type of sensor is a glucose or lactate sensor which includes an enzyme (e.g., glucose oxidase, glucose dehydrogenase, lactate oxidase, and the like) in the sensing layer. The glucose or lactate may react with a second compound in the presence of the enzyme. The second compound may then be electrooxidized or electroreduced at the electrode. Changes in the signal at the electrode indicate changes in the level of the second compound in the fluid and are proportional to changes in glucose or lactate level and, thus, correlate to the analyte level.

In certain embodiments which include more than one working electrode, one or more of the working electrodes do not have a corresponding sensing layer, or have a sensing layer which does not contain one or more components (e.g., an electron transfer agent and/or catalyst) needed to electrolyze the analyte. Thus, the signal at this working electrode corresponds to background signal which may be removed from the analyte signal obtained from one or more other working electrodes that are associated with fully-functional sensing layers by, for example, subtracting the signal.

In certain embodiments, the sensing layer includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic or organometallic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, or derivatives thereof The electron transfer agents may also have one or more ligands covalently bound in a polymer, each ligand having at least one nitrogen-containing heterocycle, such as pyridine, imidazole, or derivatives thereof.

The present disclosure may employ electron transfer agents having a redox potential ranging from about −100 mV to about +150 mV versus the standard calomel electrode (SCE), e.g., ranges from about −100 mV to about +150 mV, e.g., ranges from about −50 mV to about +50 mV, e.g., electron transfer agents have osmium redox centers and a redox potential ranging from +50 mV to −150 mV versus SCE.

The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone glucose dehydrogenase (PQQ)), or oligosaccharide dehydrogenase, may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent (which, as described above, may be polymeric). A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

Certain embodiments include a Wired Enzyme™ sensing layer that works at a gentle oxidizing potential, e.g., a potential of about +40 mV. This sensing layer uses an osmium (Os)-based mediator designed for low potential operation and is stably anchored in a polymeric layer. Accordingly, in certain embodiments the sensing element is a redox active component that includes (1) Osmium-based mediator molecules attached by stable (bidente) ligands anchored to a polymeric backbone, and (2) glucose oxidase enzyme molecules. These two constituents are crosslinked together.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may serve many functions, e.g., functionalities of a biocompatible layer and/or interferent-eliminating layer may be provided by the mass transport limiting layer.

In certain embodiments, a mass transport limiting layer is a membrane composed of crosslinked polymers containing heterocyclic nitrogen groups, such as polymers of polyvinylpyridine and polyvinylimidazole. Electrochemical sensors equipped with such membranes have considerable sensitivity and stability, and a large signal-to-noise ratio, in a variety of conditions.

According to certain embodiments, a membrane is formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A biocompatible layer (not shown) may be provided over at least that portion of the sensor which is subcutaneously inserted into the patient. The biocompatible layer may be incorporated in the interferent-eliminating layer or in the mass transport limiting layer or may be a separate layer. The layer may prevent the penetration of large biomolecules into the electrodes. The biocompatible layer may also prevent protein adhesion to the sensor, formation of blood clots, and other undesirable interactions between the sensor and body. For example, a sensor may be completely or partially covered on its exterior with a biocompatible coating.

An interferent-eliminating layer (not shown) may be included in the sensor. The interferent-eliminating layer may be incorporated in the biocompatible layer or in the mass transport limiting layer or may be a separate layer. Interferents are molecules or other species that are electroreduced or electrooxidized at the electrode, either directly or via an electron transfer agent, to produce a false signal. In one embodiment, a film or membrane prevents the penetration of one or more interferents into the region around the working electrode. In many embodiments, this type of interferent-eliminating layer is much less permeable to one or more of the interferents than to the analyte. An interferent-eliminating layer may include ionic components to reduce the permeability of the interferent-eliminating layer to ionic interferents having the same charge as the ionic components. Another example of an interferent-eliminating layer includes a catalyst for catalyzing a reaction which removes interferents.

A sensor may also include an active agent such as an anticlotting and/or antiglycolytic agent(s) disposed on at least a portion of a sensor that is positioned in a user. An anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents. Embodiments may include an antiglycolytic agent or precursor thereof The term "antiglycolytic" is used broadly herein to include any substance that at least retards glucose consumption of living cells.

Sensors described herein may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors. Calibration may be accomplished using an in vitro test strip or other calibrator, e.g., a small sample test strip such as a test strip that requires less than about 1 microliter of sample (for example FreeStyle® blood glucose monitoring test strips from Abbott Diabetes Care Inc.). For example, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is obtained firstly. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate.

An analyte system may include an optional alarm system that, e.g., based on information from a processor, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels reach or exceed a threshold value. An alarm system may also, or alternatively, be activated when the rate of change or acceleration of the rate of change in analyte level increase or decrease reaches or exceeds a threshold rate or acceleration. For example, in the case of a glucose monitoring system, an alarm system may be activated if the rate of change in glucose concentration exceeds a threshold value which might indicate that a hyperglycemic or hypoglycemic condition is likely to occur. A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

The subject disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a transmitter, a receiver/display unit, and a drug administration system. In some cases, some or all components may be integrated in a single unit. The sensor-based drug delivery system may use data from the one or more sensors to provide necessary input for a control algorithm/mechanism to adjust the administration of drugs, e.g., automatically or semi-automatically. As an example, a glucose sensor could be used to control and adjust the administration of insulin from an external or implanted insulin pump.

Returning to the Figures, as discussed above the sensitivity associated with the analyte sensor may be attenuated during the first 24 hours or so following the sensor insertion due to, for example, tissue trauma, and the like, potentially resulting in ESA condition for the analyte sensor. Accordingly, in accordance with embodiments of the present disclosure, analyte sensor calibration management is provided to effectively detect the occurrence of the sensor ESA condition, properly categorizing it and thereafter, managing the ESA condition such that potentially false readings from the sensor are minimized while the time period by which the reporting of the monitored analyte level from the sensor is initiated as close to the initial sensor insertion as possible.

In one aspect, the analyte sensor calibration management routine may be configured to detect the presence of ESA condition, confirm the detected ESA event, and to manage calibration during the confirmed ESA event to ensure optimal calibration sensitivity estimate.

In one aspect, the analyte sensor calibration management algorithm includes three parts: (1) ESA detection, (2) ESA categorization, and (3) ESA management. Each aspect or part of the management algorithm is discussed in detail below.

In one aspect, the ESA detection component of the calibration management algorithm includes detection of the sensor signal (for example, the raw current signal from the analyte sensor) and evaluating it for characteristics of ESA condition. If ESA condition is detected based on this evaluation, a calibration of the analyte sensor is requested (for example, by prompting the user to perform a fingerstick measurement and enter the resulting reference blood glucose measurement value) to obtain a sensitivity used to confirm the ESA event.

The ESA categorization aspect of the sensor calibration management routine in one aspect of the present disclosure includes rating the severity of the possible attenuation in the analyte sensor signal based on the sensitivities from the calibration measurements. In one aspect, the ESA categorization routine may classify the sensor signal characteristics into one of three categories: (a) No ESA (0), (b) Possible ESA (1), or (c) Likely ESA (2), based upon which, the ESA management component of the calibration management event routine, in one aspect, performs additional processing to, for example, output the resulting monitored analyte level (for example, on the display of the receiver unit 104/106 (FIG. 1)), or request additional reference blood glucose measurements within a given time period, to verify that the ESA condition is no longer present or insignificant.

More specifically, the ESA management routine of the calibration management algorithm, in one aspect, may be configured to either update the calibration sensitivity and report or display the monitored analyte level from the sensor, update the calibration sensitivity and temporarily report the monitored analyte level, or suspend reporting of the monitored analyte level, based, at least in part, on the ESA categorization routine. In this manner, in one aspect of the present disclosure, there is provided an effective sensor calibration management approach that optimizes the analyte monitoring system accuracy and improves user experience, based on, for example, maximizing data yield (reporting the monitored glucose level as early as possible from the initial insertion), while minimizing the number of necessary calibration attempts (for example, the need to perform in vitro blood glucose testing).

More specifically, in one aspect, the ESA detection routine of the calibration management algorithm may be configured to detect possible ESA events by evaluating various signal characteristics, including sensor output, temperature, and/or elapsed time from sensor insertion. The ESA detection routine in one aspect evaluates the sensor signal for characteristics similar to those present or associated with ESA events, including, for example a depression or attenuation in the sensor signal during the first 24 hours. The threshold for the ESA detection routine may vary according to apriori knowledge of how the probability of the ESA event may be correlated to other measurable quantities, and/or according to real-time revision of the likelihood of the ESA event itself. An example of apriori knowledge may include the correlation of the probability of the ESA condition to elapsed time since the start of sensor life (i.e., sensor insertion).

When the ESA detection routine determines that there is a high probability that the sensor output is exhibiting ESA condition characteristics, in one aspect, another calibration measurement (i.e., fingerstick test) may be requested to be used to categorize and confirm the ESA event. The calibration request timing and the sensor signal reporting following the ESA condition detection may vary depending on the certainty or the likelihood of the ESA condition presence based on the ESA detection routine.

For example, in one embodiment, if the ESA detection routine determines that the probability of ESA condition is high, then calibration may be requested immediately (for example, by prompting the user to perform another fingerstick test) and provide the reference blood glucose measurement value obtained, and the sensor representing the monitored analyte level are not reported to the user, but rather, withheld (for example, by disabling, suspending or deactivating the display in the receiver unit 104/106) until a calibration measurement can be performed to confirm the presence of ESA condition. On the other hand, if the ESA detection routine determines that the likelihood of the presence of ESA condition is less certain, sensor data corresponding to the monitored analyte level may be reported or displayed to the user on a conditional basis, and additional calibrations may be requested at a later scheduled time if the attenuated signal characteristics (potentially indicating a likelihood of ESA condition) persist for a predetermined time period.

The ESA categorization routine of the analyte sensor calibration management algorithm in one aspect, may be configured to categorize the sensor signal characteristics into three levels that are based on the confidence in the existence of ESA condition for the sensor. The routine may be configured to assess the sensor signal by looking at the magnitude of the raw sensor signal (Sr), as well as the sensitivity of the sensor signal obtained from a reference glucose measurement, for which both magnitude (Si) and variation (dSi) from previous reference measurements are considered. Thresholds for each signal measurement (Sr, Si and dSi), assigned for each of the three algorithm categorization levels (0, 1 or 2), may be checked to assign the sensitivity to one of the three ESA categories.

The three categories indicate the confidence level or the likelihood that ESA condition is present for the analyte sensor. For example, No ESA (level 0) indicates that there is no likelihood that ESA condition is present for the sensor. Possible ESA (level 1) indicates that there may be a possibility of ESA condition present for the sensor at this calibration event. Further, Likely ESA (level 2) indicates that it is likely there is ESA condition present for the sensor at the current calibration event. The checks for these measurements are performed at each calibration measurement, for example, when the user performs a fingerstick test to provide the reference blood glucose measurement, resulting in the appropriate categorization for each calibration event. Since the probability of the ESA signal characteristic varies with elapsed time from the initiation of sensor wear, the thresholds for the ESA categorization routine may vary over time. The thresholds may also vary based on the outcome of previous calibration measurements for any given sensor, since the probability that a given calibration will result in a detection of ESA increases when a signal perturbation has been previously observed for the sensor.

The ESA management routine of the sensor calibration management algorithm in one aspect of the present disclosure has three outcomes that are based on the level of confidence in the presence of ESA condition for the sensor. For calibrations that are categorized as having No ESA (level 0), it is not likely that an ESA event will result in inaccurate results, and therefore, the sensor data corresponding to the monitored analyte level are determined and reported based on the sensitivity obtained from the calibration event.

For calibrations that are categorized as Possible ESA (level 1), the sensitivity estimate may likely be valid for a limited time period, and therefore, the sensor data corresponding to the monitored analyte level may be determined and reported to the user based on the sensitivity obtained from the calibration event on a probationary basis (for a predetermined time period such as, for example, two hours or any other suitable probationary time period), after which the user may be prompted to perform another calibration to confirm the continued validity of the sensitivity obtained from calibration.

For calibrations categorized as Likely ESA (level 2), it is highly likely that the sensor data corresponding to the monitored analyte level will include substantial attenuation or error, and therefore, the reporting or output of the sensor data is suspended for a predetermined wait period during which the sensor signal is allowed to recover (for example, from the temporary attenuation). At the end of the predetermined wait time period, the user may be requested to perform another fingerstick test to perform another calibration to verify that ESA condition is no longer present or that it is insignificant.

In this manner, in accordance with various embodiments of the present disclosure, analyte sensor calibration management is provided which effectively processes the analyte sensor signals to maximize the accurate reporting of the monitored analyte level while minimizing the potential for providing false or erroneous readings from the sensor during the occurrence of signal attenuation events.

In one aspect of the present disclosure, the routines and algorithms described herein may be incorporated in the receiver unit 104/106, the data processing unit 102, or the data processing terminal/infusion section 105 of the analyte monitoring system 100 (FIG. 1). More specifically, in accordance with the embodiments of the present disclosure, there may be provided one or more signal detectors configured to perform some, shared or all of the routines described herein to management sensor calibration for the ESA detection, the ESA categorization, and the ESA management, by for example, one or more processors, state machines and the like which may include integrated circuits, application specific integrated circuits (ASIC), and/or combination of hardware and software components including memory devices such as random access memory (RAM), read only memory (ROM), solid state drives, and the like.

More specifically, in one embodiment, a plurality of signal detectors may be used to implement the calibration management routine described herein. A first signal detector may be configured for detection of ESA state based on blood glucose measurements or other reference information and the analyte sensor data from the sensor analyte monitoring system. The outcome of a first signal detector may be configured to determine whether the monitored sensor signal from the analyte monitoring system is in ESA condition.

A second signal detector may be configured to monitor the analyte monitoring system sampled data (for example, one minute data, or any suitable sampling rate). In one aspect, a second signal detector may be configured to instruct the analyte monitoring system to prompt the user to enter an immediate or scheduled blood glucose measurement (for example, based on a fingerstick test using a blood glucose meter) to confirm whether an ESA condition exists, and to be used in conjunction with the first signal detector—i.e., the detection of ESA state of the analyte monitoring system based on the reference blood glucose measurements.

In one aspect, the first and second signal detectors are configured to generate one of a plurality, e.g., three, ESA levels—level 0: no ESA, level 1: possible ESA, and level 2: likely ESA. As discussed above, in one aspect, the level 1 condition associated with possible ESA state of the sensor may be characterized as no significant signal attenuation but based on the detected or monitored conditions associated with the sensor, a verification of the potential ESA condition is desired or necessary within a predetermined period, such as, two hours (or any other suitable time period).

First Signal Detector and ESA Categorization Module

The fingerstick test (or reference blood glucose measurement)-based ESA detector (ESA_FS) operates when a calibration attempt passes a data condition verification routine during the active ESA detection phase. More specifically, the ESA_FS detector starts its activity at the first baseline calibration (for example, at about one hour or less from the time of sensor insertion). It remains active during the initial phase of the sensor life (for example, approximately the first 24 hours from initial insertion) when the likelihood of ESA condition is greatest.

In one embodiment, the first signal detector takes the role of "ESA Categorization" module 620 (FIG. 6) during active ESA condition detection phase. In addition, if other signal detectors do not suspect ESA condition, but an eligible fingerstick blood glucose measurement is made during the active ESA condition detection phase, the first signal detector also takes the role of "ESA Detection" module 610.

The ESA_FS detector uses two tests, one relative and one absolute, either of which can detect signal attenuation levels (ESA_FS level) based on any reference blood glucose measurement within the active ESA detection phase. The higher of the two levels may be chosen if they are not the same for the two tests. More specifically, in one embodiment, the relative test compares the value of the latest immediate sensitivity based on the latest fingerstick blood glucose test, $S_i(k)$, to the values of the previous immediate sensitivity, $S_i(k-1)$, and the most recent immediate sensitivity used to calculate the composite sensitivity, $S_i(m)$. The values $S_i(k)$, $S_i(k-1)$, and $S_i(m)$ are selected such that calibration post condition verifications pass at those instances (at time index k, k−1, and m). In one aspect, manual calibrations are subject to the tests performed by the ESA_FS detector, but the resulting immediate sensitivities may not be used as previous values.

Based on the relative test, two ratios are formed, $S_i(k)/S_i(k-1)$, and $S_i(k)/S_i(m)$. The two threshold values of ESA_FS levels are assigned using these ratios as follows:

(1) ESA_FS level 2 (likely ESA condition) if:

$$S_i(k)/S_i(k-1) < K_{lo\_Rel\_ESA\_FS[2]},$$
$$\text{OR } S_i(k)/S_i(m) < K_{lo\_Rel\_ESA\_FS\_Cal[2]},$$

(2) ESA_FS level 1 (possible ESA condition) if NOT ESA_FS level 2 AND:

$$S_i(k)/S_i(k-1) < K_{lo\_Rel\_ESA\_FS[1]},$$
$$\text{OR } S_i(k)/S_i(m) < K_{lo\_Rel\_ESA\_FS\_Cal[1]},$$

where $K_{lo\_Rel\_ESA\_FS[2]}$ is less than or equal to $K_{lo\_Rel\_ESA\_FS[1]}$, and further, $K_{lo\_Rel\_ESA\_Cal[2]}$ is less than or equal to $K_{lo\_Rel\_ESA\_Cal[1]}$, and further, where each of these parameters may be predetermined values (for example, set at 0.5 or 0.75 or other suitable value) programmed or programmable in the receiver unit 104/106 (FIG. 1) of the analyte monitoring system, for example.

Otherwise, the relative test of ESA_FS generates a level 0 output indicative of absence of ESA condition.

In accordance with aspects of the present disclosure, the absolute test compares the sensitivity level $S_i(k)$ to sensitivity thresholds scaled to the analyte sensor nominal sensitivity $S_{nom}$. As in the relative test, $S_i(k)$ may be chosen such that it passes calibration post condition verifications. ESA_FS levels are assigned as follows:

ESA_FS level 2 (likely ESA condition) if: $S_i(k)/S_{nom} < K_{min\_Abs\_ESA\_FS[2]}$ ESA_FS level 1 (possible ESA condition) if NOT ESA_FS level 2 AND:

$$S_i(k)/S_{nom} < K_{min\_Abs\_ESA\_FS[1]},$$

where $<K_{min\_Abs\_ESA\_FS[2]}$ is less than equal to $K_{min\_Abs\_ESA\_FS[1]}$, and further, each of these two parameters may be predetermined or programmed.

Otherwise, the absolute test of ESA_FS generates a level 0 output (indicating no detected ESA condition).

The threshold values for the relative and absolute tests above may be valid when the likelihood of ESA condition is the greatest. When the ESA detectors remain active beyond that time up to an absolute latest time beyond which the ESA detection will be ignored by the system, the likelihood of ESA may be assumed to be correlated to the elapsed time since sensor insertion, and that different likelihoods allow for different tradeoffs between maximizing ESA detection and minimizing the number of calibration requests.

Second Signal Detector

The second signal detector in the analyte monitoring system is based on inferring ESA condition from the analyte sensor signal characteristics. One example of a signal characteristic is the detection of low glucose values. When this detector reports a nonzero ESA level (for example, presence of signal attenuation (ESA)), there are two possibilities: either the system is in ESA, or the user is in (or near) hypoglycemia.

In one embodiment, the second signal detector may be configured to include the functions of the "ESA Detection" module 610 (FIG. 6), and is not used solely to categorize the detected ESA condition for the "ESA Management" module 630 of the overall system. When the second signal detector produces a nonzero output, a reference blood glucose measurement is expected in a manner determined by the "ESA Management" module 630 of the overall system.

To minimize the effect of noise, a predefined number of the most recent unfiltered glucose samples from the analyte sensor, $G_{CAL}$, are averaged to derive at the glucose value $G_{ESA\_CGM}$.

The detector reports one of three possible ESA levels based on the glucose value $G_{ESA\_CGM}$:

ESA level 2 (likely ESA condition) if: $G_{ESA\_CGM} < G_{min\_ESA\_CGM[2]}$

ESA level 1 (possible ESA condition) if NOT ESA_FS level 2 AND:

$$G_{ESA\_CGM} < G_{min\_ESA\_CGM[1]}$$

where $G_{min\_ESA\_CGM[2]}$ is less than or equal to $G_{min\_ESA\_CGM[1]}$, and further, correspond to predetermined values or parameters programmed into the system.

Otherwise, the absolute test of ESA generates a level 0 output indicating no detected ESA condition. Furthermore, if all of the most recent predefined number of unfiltered glucose sample $G_{CAL}$ is not available, the second signal detector may be configured to report a zero level.

ESA Event Manager

Figure 6:
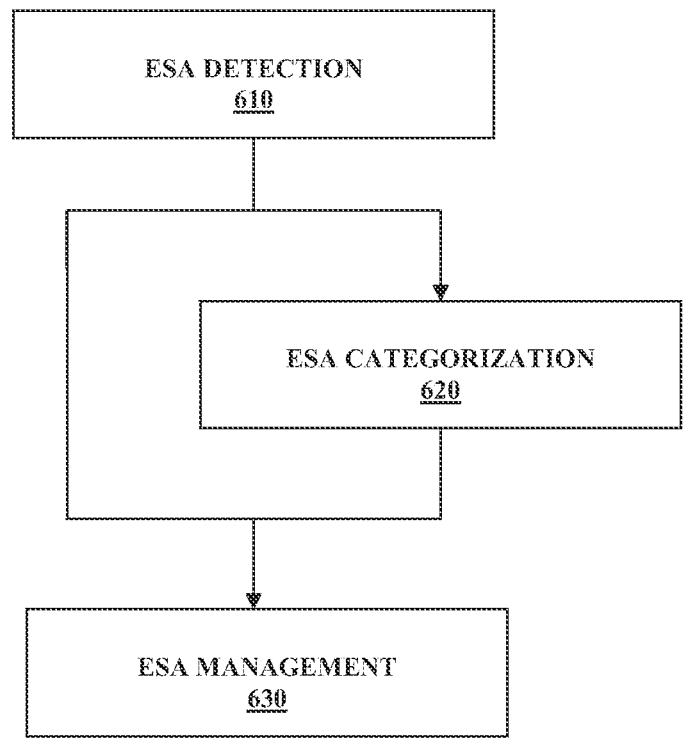
FIG. 6 is a flowchart illustrating an overall analyte sensor calibration management in accordance with one embodiment of the present disclosure.

In one embodiment, different roles of the first signal detector and the coexistence of the second signal detector may be managed by the "ESA Management" module 630 (FIG. 6). The ESA management may be influenced by the sensitivity and specificity of each detector, the history of past or prior calibration events and reference blood glucose measurement timing, the scheduled calibration events in the near future, and other aspects including usability.

In the case where the sensor is in the level 0 condition indicating absence of ESA condition, the second signal detector may be configured to begin to operate after the second baseline calibration (that is, the second scheduled calibration time period for the analyte sensor) which may be a floating calibration event (measured from when the no ESA condition is determined) scheduled following the first absolute calibration (measured from the initial sensor insertion event) and thereby reporting measured glucose levels to the user. In one aspect, the display or output of the measured glucose levels may be suspended at a predetermined time associated with the earliest allowable termination of the signal detectors in the system.

In order to avoid closely spaced fingerstick blood glucose measurements, in one aspect, the output from the second signal detector may be ignored when either less than a predefined idle time period has elapsed after a successful baseline calibration where asynchronous stability request is not allowed (for example, 30 minutes) after any calibration attempt, or when less than a predefined idle time period has elapsed prior to the next scheduled baseline calibration where asynchronous stability request is not allowed (for example, 30 minutes) before any scheduled calibration attempt.

In one aspect, during active ESA detection phase, the first signal detector is used to determine whether ESA condition is present or absent. In one embodiment, it is assumed that ESA condition is absent at the sensor start—that is, when the sensor is initially inserted. The transition, behavior, and retention of the states in one aspect are described below. For example, in one aspect, transition into a determination that ESA condition is present occurs when the latest ESA_FS level is determined to be greater than the largest allowable output level from the first signal detector of prior measurements that is considered as an indication of being free from early signal attenuation. For example, in the case where level 0 and level 1 are considered not sufficiently stringent for attenuation mitigation, in one aspect of the present disclosure, only level 2 may be configured to trigger the transition to a state where it is determined that ESA condition is present.

When the analyte monitoring system determines that the sensor is in ESA condition, in one aspect, the receiver unit 104/106 (FIG. 1) may be configured to disable the output or display of the measured or detected glucose level. Moreover, the receiver unit 104/106 may be configured to maintain the disabled (or suspended or deactivated) output/display for a predefined idle time period after the presence of ESA condition has been confirmed by the reference blood glucose measurement before the user is prompted for another confirmation (for example, by requesting another fingerstick test) before transitioning to the state with confirmed no ESA condition.

Furthermore, in yet another aspect, receiver unit 104/106 may be configured to not request a stability calibration verification while sensor is in ESA condition. However, any user-motivated or self-initiated fingerstick blood glucose measurement may be used, if confirmed, to transition into a state where ESA condition is absent. Also, when the sensor is deemed to be in the confirmed no ESA condition, the second signal detector shows a level 0 (reflecting a no ESA condition), and signal precondition verification passes, the receiver unit 104/106 (FIG. 1) of the analyte monitoring system may be configured to request a reference blood glucose measurement to confirm that the absence of ESA condition is complete and/or to initiate calibration.

In one aspect, transition into a state associated with absence of ESA condition occurs when a new fingerstick blood glucose measurement shows an ESA_FS level (for example, the output of the first signal detector discussed above) that is less than or equal to the largest allowable output level from the first signal detector of prior measurements that is considered as an indication of being free from early signal attenuation. A successful calibration is required for glucose results to be reported or displayed, for example.

When it is determined that ESA condition is absent, the sensor signals, in one aspect may be further processed to determine stability and possible errors. For example, in one aspect, when a level 2 output (i.e., likely ESA condition) from the second signal detector occurs for the first time, an immediate request for a stability calibration may be generated. After the first occurrence of level 2 output from the second signal detector, the analyte sensor signals are checked at the time intervals (for example, approximately 1 to 2 hours, or other suitable time interval) since the last reference blood glucose measurement with stability verification routine before another measurement is requested, after the most recent successful calibration. Further, a nonzero level (i.e., a level 1 or level 2—possible or likely ESA condition) triggers a stability calibration request. Also, in one aspect, if a previous ESA_FS level is greater than 0, a reference blood glucose measurement is requested at a time interval since the last blood glucose measurement, and ESA_FS is determined using the new reference measurement.

Referring now to the Figures, FIG. 6 is a flowchart illustrating an overall analyte sensor calibration management in accordance with one embodiment of the present disclosure. As shown, analyte sensor calibration management system in accordance with one aspect of the present disclosure includes an ESA detection module 610, and ESA categorization module 620, and an ESA management module 630. As discussed above, the ESA detection module 610 is configured to detect the occurrence of an early signal attenuation event during the initial time period following the analyte sensor insertion or wear, for example, the first 24 hour period measured from the initial sensor insertion.

When signal attenuation associated with an analyte sensor is detected, the ESA categorization module in one embodiment is configured to properly categorize the detected signal attenuation condition. Thereafter, depending upon the type of ESA condition detected—for example, no ESA condition detection, likely ESA condition detection, or possible ESA condition detection, the ESA management module 630 is configured to initiate one or more processes to confirm the detected and categorized signal attenuation condition. And further, to perform additional processing to effectively manage the calibration algorithm associated with the analyte sensor operation such that maximum reportable data yield may be attained, providing improved usability of the analyte sensor for continuously or intermittently monitoring and outputting monitored analyte level such as the fluctuation in the glucose level of a patient or a user.

Figure 7:
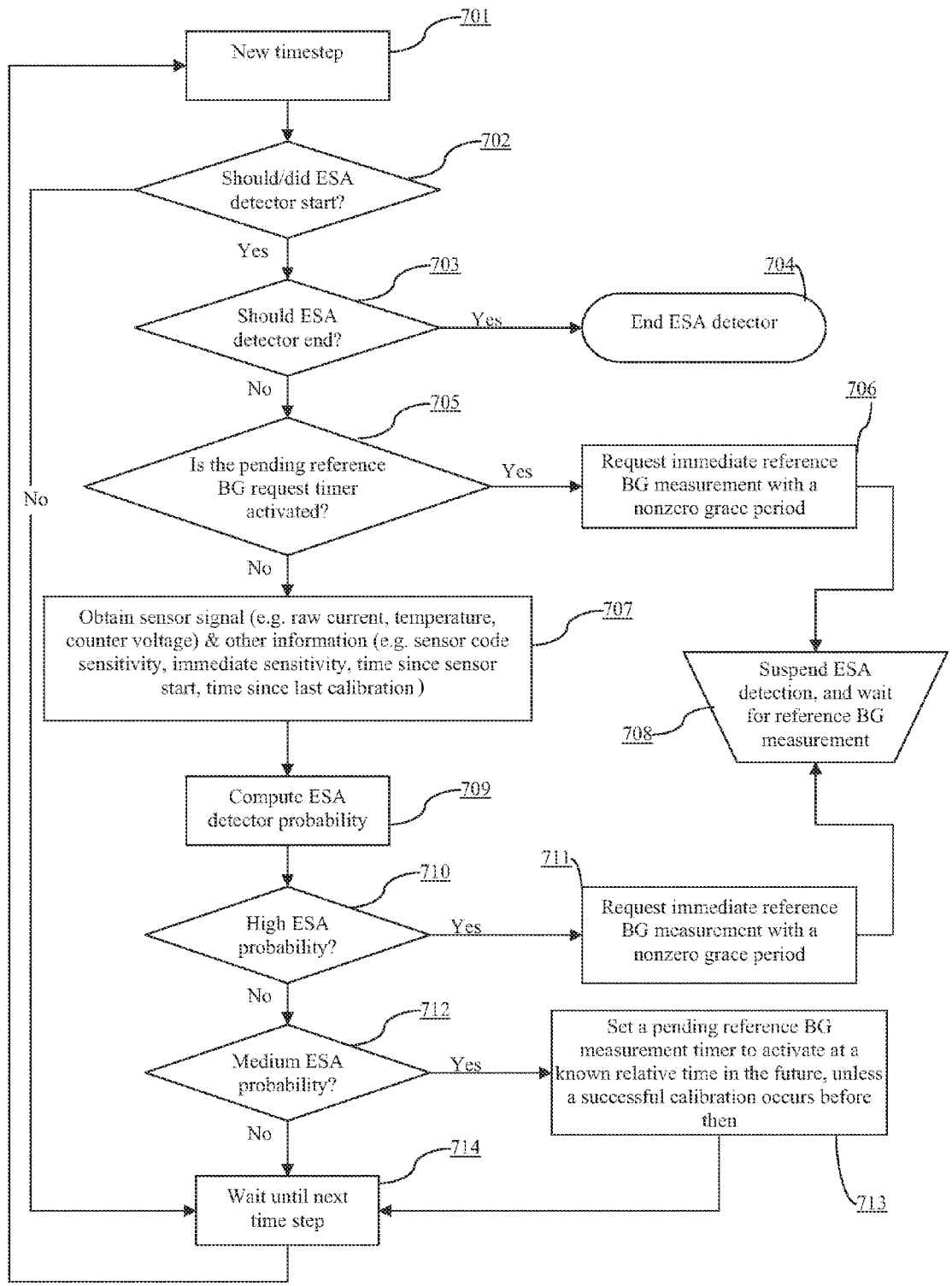
FIG. 7 is a flowchart illustrating early signal attenuation (ESA) detection routine of FIG. 6 in accordance with one aspect of the present disclosure.

FIG. 7 is a flowchart illustrating early signal attenuation (ESA) detection routine of FIG. 6 in accordance with one aspect of the present disclosure. Referring to FIG. 7, the ESA detection routine executed by the ESA detection module 610 (FIG. 6), for example, is described. More specifically, for each monitored signal from the analyte sensor (such as for each one minute data from the analyte sensor), a new timestep is initiated (701), and it is determined whether ESA detector should be or has started (702). If it is determined that the ESA detector has not or should not be started, then the routine waits for the next time step (714) based on the next signal received from the sensor (for example, the subsequent one minute signal received from the analyte sensor).

Referring to FIG. 7, if it is determined that ESA detector should or did start (702), then it is determined whether it should be terminated (703). If it is determined that the ESA detector should be terminated (703), then the routine ends (704). However, if it is determined that the ESA detector should not terminate (703), then it is determined whether a pending reference blood glucose measurement request timer has been activated (705). If it is determined that the pending reference blood glucose measurement request timer has been activated (705), then in one embodiment, a reference blood glucose measurement request is generated and output to the user with a nonzero grace period (706). Thereafter, the ESA detector is suspended and the system awaits for the requested reference blood glucose measurement (708).

On the other hand, if it is determined that the pending reference blood glucose measurement request timer is not activated (705), then analyte sensor signal information as well as other relevant information is retrieved or obtained (707). That is, for example, the sensor raw current signal, the associated temperature information, sensor counter voltage data, for example, are obtained, in addition to other relevant information such as, for example, the sensor code sensitivity, immediate sensitivity, time duration elapsed since the sensor insertion, and time elapsed since the prior sensor calibration event, for example. Within the scope of the present disclosure, other relevant data related to the operation and characteristics of the analyte sensor may be obtained.

Referring still to FIG. 7, thereafter, the probability or ESA condition presence is determined (709), the result of which is compared to one or more threshold values to determine whether high ESA condition probability exists (710). If it is determined that high ESA condition probability exists, then reference blood glucose measurement data is requested with a nonzero grace period (711), and the ESA detection routine is suspended to await for the requested reference blood glucose measurement data. On the other hand, if it is determined that high ESA condition probability does not exist (710), then it is determined whether medium ESA condition probability exists (712). If it is determined that medium ESA condition probably does not exist, then the routine proceeds to wait for the next sensor data (714). On the other hand, if it is determined that medium ESA condition probability exists (712), then a pending reference blood glucose measurement timer is set to activate at a predetermined relative time in the future, unless a successful calibration event is detected prior to the expiration of the activated timer (713).

In the manner described above, in one embodiment of the present disclosure, the ESA detection module 610 (FIG. 6) may be configured to detect attenuation in analyte sensor signal during the initial time period from the sensor insertion.

Figure 8:
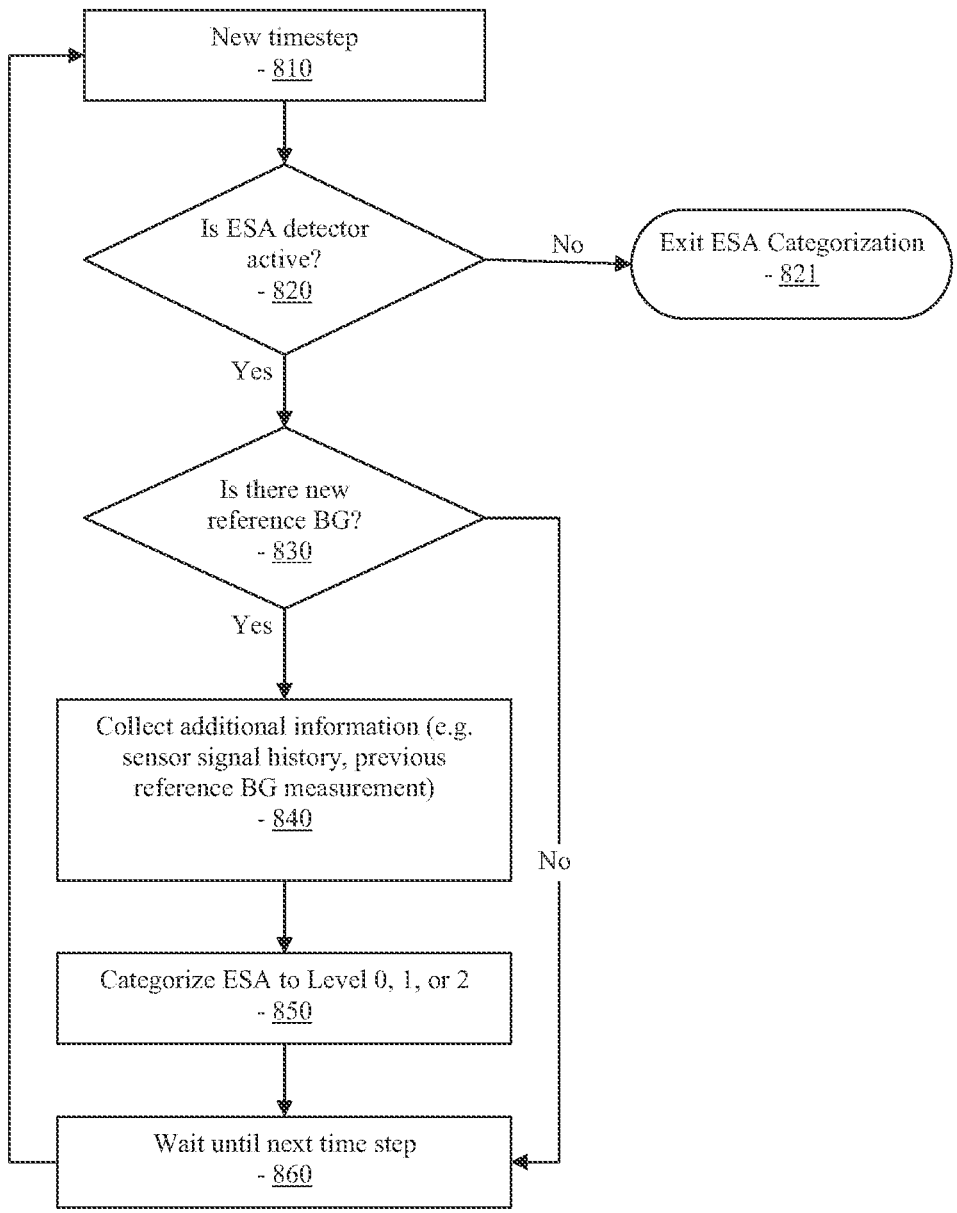
FIG. 8 is a flowchart illustrating early signal attenuation (ESA) categorization routine of FIG. 6 in accordance with one aspect of the present disclosure.

Referring back to the Figures, FIG. 8 is a flowchart illustrating early signal attenuation (ESA) categorization routine of FIG. 6 in accordance with one aspect of the present disclosure. As described in detail above, upon detection of a signal attenuation occurrence associated with an analyte sensor, the detected attenuation is categorized by, for example, the ESA categorization module (620). More specifically, referring now to FIG. 8, for each new timestep associated with the detection of the one minute sensor signal from the analyte sensor, for example (810), it is determined whether ESA detector is active (820). If it is determined that the ESA detector is not active (or the ESA routine is not activated or initiated), then the ESA categorization routine terminates (821).

On the other hand, if it is determined that the ESA detector is active (820), then it is determined whether a new reference blood glucose measurement is available (830). If the reference blood glucose measurement is not available, then the routine terminates and waits for the next analyte sensor signal (860). If it is determined, however, that the reference blood glucose measurement is available (830), then analyte sensor related information is retrieved and/or collected (840). In one embodiment, analyte sensor related information may include, for example, sensor signal history, previous reference blood glucose measurement values, calibration time period, and the like. Thereafter, the detected signal attenuation is categorized into one of three categories—level 0, level 1, and level 2 (850), corresponding to no ESA condition, possible ESA condition, and likely ESA condition, respectively and as discussed in detail above. In one embodiment, after categorization, the routine proceeds to the ESA management module (630) (FIG. 6) and also, repeats the same categorization procedure for the next received sensor signal (860).

Figure 9:
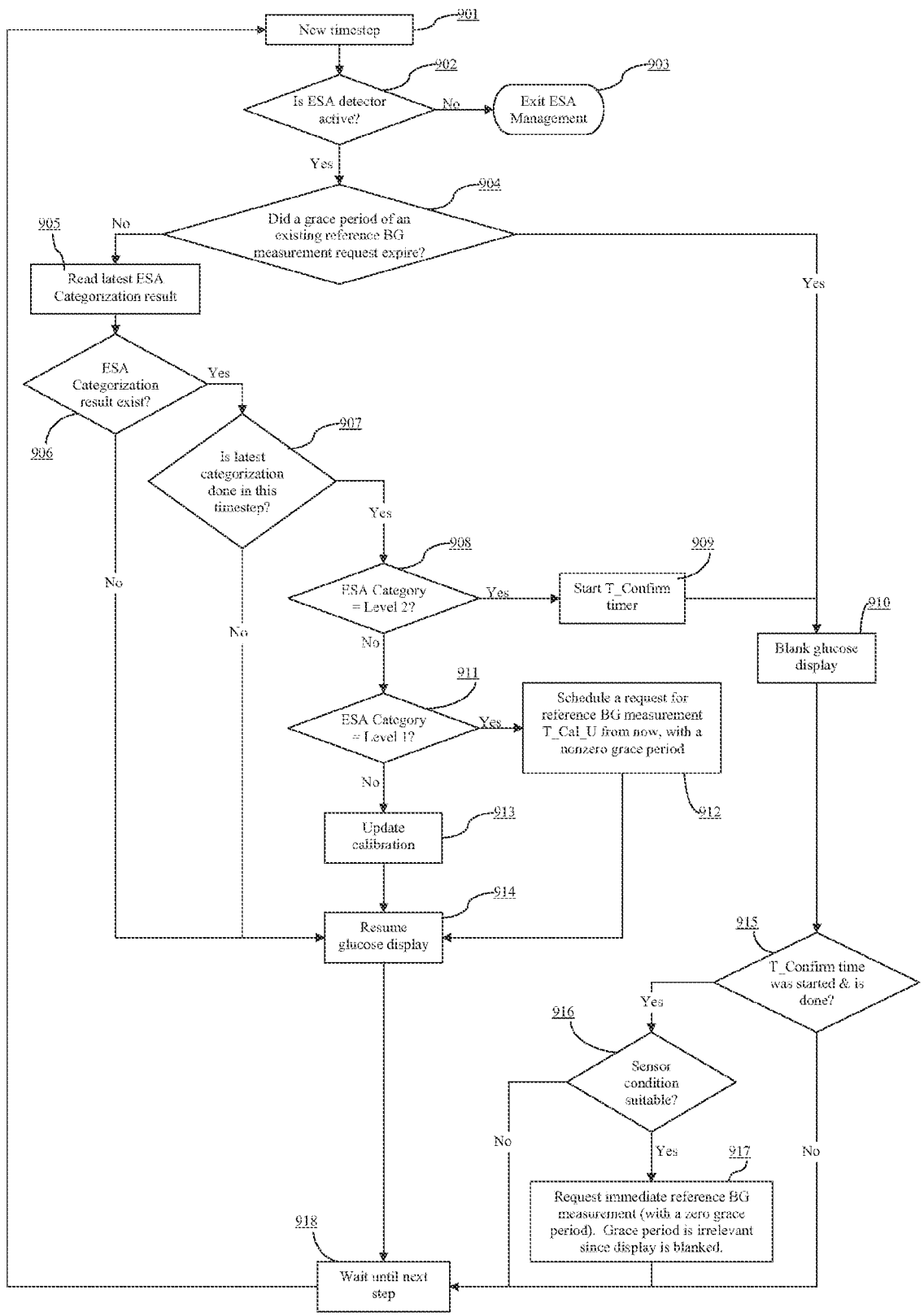
FIG. 9 is a flowchart illustrating early signal attenuation (ESA) management routine of FIG. 6 in accordance with one aspect of the present disclosure.

Referring back, as discussed, after performing ESA condition categorization (620) (FIG. 6), in one aspect, the ESA condition management routine is initiated (630). More specifically, FIG. 9 is a flowchart illustrating early signal attenuation (ESA) management routine of FIG. 6 in accordance with one aspect of the present disclosure. As shown, for each analyte sensor signal received or detected (901), it is first determined whether the ESA detector is active (902). If it is determined that the ESA detector is not active, then the ESA management routine terminates (903).

On the other hand, if it is determined that the ESA detector is active, then it is determined whether a grace period of an existing reference blood glucose measurement request has expired (904). If it is determined that the grace period of the existing reference blood glucose measurement request has expired, then the display or reporting module associated with the output of the analyte sensor data is disabled, suspended, deactivated or otherwise blanked such that no real time glucose information is provided to the user (910). If it is determined however, that the grace period of the existing reference blood glucose measurement request has not expired, then the ESA categorization module output from the ESA categorization module (620) is retrieved (905).

Referring again to FIG. 9, it is thereafter determined whether the ESA categorization result or output exists (906). If not, then the output or reporting of the real time glucose information proceeds and the user is provided with the glucose level data (914), and thereafter waits to receive the next analyte signal associated with the next timestep (918). On the other hand, if the ESA categorization result exists (906), then it is determined whether the ESA categorization is associated with the current analyte signal (associated with the current timestep, for example) (907). If it is not associated with the current analyte signal, then the routine proceeds to displaying or outputting the monitored analyte level to the user (914), and waits to receive the next analyte signal associated with the next timestep (918).

However, if it is determined that the ESA categorization is associated with the current timestep (907), then it is determined whether the ESA condition categorization is associated with level 2 category indicating a likely ESA condition for the sensor (908). If it is determined that the ESA condition categorization is associated with level 2 category, then a timer (T_Confirm timer) is started (909) and the reporting or output of the glucose data is disabled (910). If it is determined however, that the ESA condition category is not associated with level 2 (908), then it is determined whether the categorized ESA condition is level 1 (911). If it is determined to be level 1 indicating a possible ESA condition, then a request for a blood glucose measurement is scheduled for a predetermined time period (T_Cal_U) with a nonzero grace period (912), and the real time glucose information is displayed or output to the user (914).

Referring back to FIG. 9, if it is determined that the ESA condition is not associated with a level 1 category (911), then the calibration for the analyte sensor is updated (913), and the monitored glucose level is displayed or output to the user (914), and the routine waits to receive the next analyte sensor signal (918). Referring still back to FIG. 9, after the display or output of the glucose value is disabled or blanked (910), it is determined whether the T_Confirm timer was started and the timer expired (915). If it has not expired, the routine waits to receive the next analyte signal (918). If, however, it is determined that the timer (T_Confirm) has lapsed (915), then it is determined whether the characteristics of the sensor is suitable, for example, for calibration (916). If it is determined that the sensor condition is not suitable (916), then the routine waits to receive the next analyte sensor signal (918). On the other hand, if it is determined that the sensor condition is stable (916), then a reference blood glucose measurement is requested with a zero grace period (917).

In the manner described above, in accordance with the various embodiments of the present disclosure, a method, apparatus and system for providing effective analyte sensor calibration management is described that monitors the early attenuation of sensor signals and processes the monitored signals to maximize the sensor data yield by providing as much of the useful and accurate monitored glucose level information to the user.

Results from Preliminary Studies

A preliminary study, was conducted with 48 sensor insertions in normal (N=10), T1DM (N=1) and T2DM (N=2) subjects using finger stick glucose measurements as a reference. Little deterioration of the results was observed when comparing the mean absolute relative difference (MARD) for the first 10 hours compared to the remaining 10 to 24 hours of day one of sensor use: 13.8% (12.8-14.9 95% CI) versus 12.6% (11.6-13.6 95% CI) respectively. During the first ten hours 7.5 hours±2.2 hours (average±SD) of glucose data would be available to the user substantially maximizing available data yield providing reportable glucose information shortly after the sensor insertion.

A second preliminary study included evaluation of the performance of the system described above which included two locations each with 47 subjects (aged 19-66) who wore 2 sensors (abdomen/arm). Continuous glucose readings were collected at one minute intervals from 1 hour after sensor insertion. Venous blood glucose measurements were obtained using a standard laboratory reference (YSI 2300) every 15 minutes for 26 hours across two in-clinic visits during the 5 day sensor wear. Capillary BG measurements were taken by each subject (on average 20 per day) on a separate blood glucose meter.

The mean and median absolute relative difference between the sensor system and YSI was 14.5% and 10.7% respectively. Moreover, continuous Glucose-Error Grid Analysis combining rate and point information gave 93.9% accurate readings and an additional 3.2% benign errors.

Traditional Clarke Error Grid (CEG) Zone A performance was 77.1% (6229/8084). This included periods of hypoglycemia and high rates of change of blood glucose during IV insulin challenges. When the rate of change of blood glucose was within ±1 mg/dL/min, the Zone A performance was 82.0% (4672/5699). Performance remained constant over all five days, with 80.7% of data in Zone A on day 1 and 74.1% in Zone A on day 5 (p=0.4503). Furthermore, Clarke Error Grid Zone A performance compared to capillary blood glucose measurement was 81.2% (3337/4108).

Hypoglycemic events at 70 mg/dL (n=119) were detected by threshold or projected alarm (30 minute setting) 91.6% of the time. Hyperglycemic events at 240 mg/dL (n=144) were detected by threshold or projected alarm 97.2% of the time. The threshold or projected alarm false alarm rate was 25.2% at 70 mg/dL and 21.2% at 240 mg/dL.

Based on the foregoing, the results from the second preliminary study demonstrate good performance of the FreeStyle Navigator® Continuous Glucose Monitoring System with data displayed from approximately one hour after sensor insertion over five days of sensor wear.

In the manner described above, in accordance with the various embodiments of the present disclosure, the analyte sensor calibration management minimizes the presentation of erroneous analyte sensor results due to ESA conditions, while maximizing reportable analyte sensor data for sensors that do not exhibit the ESA signal characteristic. Accordingly, in aspects of the present disclosure, the calibration management algorithm applies to any subcutaneously positioned analyte sensor which may exhibit ESA signal characteristics, and enables the management of calibration during periods when the analyte sensor sensitivity may deviate from the actual sensor sensitivity.

Accordingly, a method in one aspect includes monitoring for a signal level below a predetermined threshold associated with analyte level from an analyte sensor during a predefined time period, and reporting analyte level associated with the analyte sensor when the signal level monitored is not detected during the predefined time period.

The predefined time period may include less than approximately one hour.

In another aspect, the method may include receiving a blood glucose measurement, and calibrating the analyte sensor based on the received blood glucose measurement.

Further, the predetermined threshold may be associated with one or more of an impending hypoglycemic state, or a predefined signal attenuation level.

Also, reporting the analyte level may include one or more of storing the analyte level, confirming the analyte level, or outputting the analyte level.

The various processes described above including the processes performed by the data processing unit 102, receiver unit 104/106 or the data processing terminal/infusion section 105 (FIG. 1) in the software application execution environment in the analyte monitoring system 100 including the processes and routines described in conjunction with FIGS. 6-9, may be embodied as computer programs developed using an object oriented language that allows the modeling of complex systems with modular objects to create abstractions that are representative of real world, physical objects and their interrelationships. The software required to carry out the inventive process, which may be stored in the memory or storage device (not shown) of the data processing unit 102, receiver unit 104/106 or the data processing terminal/infusion section 105, may be developed by a person of ordinary skill in the art and may include one or more computer program products.

One embodiment of the present disclosure may include positioning an analyte sensor in fluid contact with an analyte, detecting an attenuation in a signal from an analyte sensor after positioning during a predetermined time period, categorizing the detected attenuation in the analyte sensor signal based, at least in part, on one or more characteristics of the signal, and performing signal processing to generate a reportable data associated with the detected analyte sensor signal during the predetermined time period.

The signal from the analyte sensor may be associated with a monitored analyte level.

The detected attenuation in the signal from the analyte sensor may be associated with an early signal attenuation condition.

The predetermined time period may not exceed approximately 24 hours.

Categorizing the detected analyte sensor signal attenuation may be based at least in part on a predetermined plurality of signal attenuation conditions.

In one aspect, the plurality of signal attenuation conditions may include a reportable signal condition, a conditional reportable signal condition, and an unreportable signal condition.

Another aspect may include outputting data associated with the monitored analyte level based on the detected analyte sensor signal when the detected analyte sensor signal attenuation includes a reportable signal condition or a conditional reportable signal condition.

Outputting data associated with the monitored analyte level may include outputting data for a preset time period when the detected analyte sensor signal attenuation includes the conditional reportable signal condition.

The preset time period may not exceed approximately two hours.

One aspect may include requesting a reference blood glucose measurement during the preset time period.

Another aspect may include calibrating the analyte sensor signal based at least in part on the reference blood glucose measurement received during the preset time period.

Yet another aspect, may include disabling outputting of the data associated with the monitored analyte level after the preset time period has elapsed.

Another embodiment, wherein performing signal processing may include requesting a reference data, and determining a sensitivity value associated with the analyte sensor based on the reference data.

The reference data may include an in vitro blood glucose measurement data.

One aspect may include calibrating the analyte sensor based at least in part on the determined sensitivity value.

A further embodiment of the present disclosure includes monitoring for a signal level below a predetermined threshold associated with analyte level from an analyte sensor during a predefined time period, and reporting analyte level associated with the analyte sensor when the signal level monitored is not detected during the predefined time period.

The predefined time period may be less than approximately one hour.

Another aspect may include receiving a blood glucose measurement, and calibrating the analyte sensor based on the received blood glucose measurement.

The predetermined threshold may be associated with one or more of an impending hypoglycemic state, or a predefined signal attenuation level.

Reporting the analyte level may include one or more of storing the analyte level, confirming the analyte level, or outputting the analyte level.

Yet still another aspect of the present disclosure includes inserting at least a portion of a glucose sensor beneath a skin surface of an individual, analyzing glucose-related signal from the sensor to determine sensor stability, and reporting glucose related information to the individual only when it is determined that the sensor is stable, wherein the glucose related information is not reported prior to determination that the sensor is stable.

Sensor stability may be determined using reference data.

Reference data may comprise sampling blood of the individual.

Reference data may be obtained from a glucose test strip.

One aspect may include analyzing the sensor signal to determine whether there exists a decrease in sensor signal.

The analyte sensor may report the glucose related information in about one hour following the insertion.

An apparatus in accordance with still another aspect may include a data communication interface, one or more processors operatively coupled to the data communication interface, and a memory for storing instructions which, when executed by the one or more processors, causes the one or more processors to position an analyte sensor in fluid contact with an analyte, detect an attenuation in a signal from an analyte sensor after positioning during a predetermined time period, categorize the detected attenuation in the analyte sensor signal based, at least in part, on one or more characteristics of the signal, and perform signal processing to generate a reportable data associated with the detected analyte sensor signal during the predetermined time period.

The signal from the analyte sensor may be associated with a monitored analyte level.

The detected attenuation in the signal from the analyte sensor may be associated with an early signal attenuation condition.

The predetermined time period may not exceed approximately 24 hours.

In one aspect, the memory for storing instructions which, when executed by the one or more processors, may cause the one or more processors to categorize the detected analyte sensor signal attenuation based at least in part on a predetermined plurality of signal attenuation conditions.

The plurality of signal attenuation conditions may include a reportable signal condition, a conditional reportable signal condition, and an unreportable signal condition.

In another aspect, the memory for storing instructions which, when executed by the one or more processors, may cause the one or more processors to output data associated with the monitored analyte level based on the detected analyte sensor signal when the detected analyte sensor signal attenuation includes a reportable signal condition or a conditional reportable signal condition.

In yet another aspect, the memory for storing instructions which, when executed by the one or more processors, may cause the one or more processors to output data for a preset time period when the detected analyte sensor signal attenuation includes the conditional reportable signal condition.

Furthermore, the preset time period may not exceed approximately two hours.

Moreover, the memory for storing instructions which, when executed by the one or more processors, may cause the one or more processors to request a reference blood glucose measurement during the preset time period.

Further, the memory for storing instructions which, when executed by the one or more processors, may cause the one or more processors to calibrate the analyte sensor signal based at least in part on the reference blood glucose measurement received during the preset time period.

Moreover, the memory for storing instructions which, when executed by the one or more processors, may cause the one or more processors to disable the outputting of the data associated with the monitored analyte level after the preset time period has elapsed.

In another aspect, the memory for storing instructions which, when executed by the one or more processors, may cause the one or more processors to request a reference data, and determine a sensitivity value associated with the analyte sensor based on the reference data.

Reference data may include an in vitro blood glucose measurement data.

Further, the memory for storing instructions which, when executed by the one or more processors, may cause the one or more processors to calibrate the analyte sensor based at least in part on the determined sensitivity value.

Moreover, in still another aspect, there is provided one or more storage devices having processor readable code embodied thereon, said processor readable code for programming one or more processors to estimate an analyte level may comprise, positioning an analyte sensor in fluid contact with an analyte, detecting an attenuation in a signal from an analyte sensor after positioning during a predetermined time period, categorizing the detected attenuation in the analyte sensor signal based, at least in part, on one or more characteristics of the signal, and performing signal processing to generate a reportable data associated with the detected analyte sensor signal during the predetermined time period.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method, comprising:
    programming a processor of an in vivo glucose monitoring system to:
       monitor a signal received from a glucose sensor positioned in fluid contact with interstitial fluid to determine if a level of the signal is below a predetermined threshold during a predefined period of time following sensor positioning;
       detect an attenuation in the signal when it is determined that the level of the signal is below the predetermined threshold during the predefined period of time following sensor positioning;
       categorize the detected attenuation in the signal based, at least in part, on one or more characteristics of the signal; and
       report information related to the signal when the level of the signal is not determined to be below the predetermined threshold during the predefined period of time following sensor positioning;
          wherein the detected attenuation in the signal is associated with an early signal attenuation condition.

2. The method of claim 1, wherein the predefined time period is within one day of sensor positioning.

3. The method of claim 2, wherein the predefined time period is within one hour of sensor positioning.

4. The method of claim 1, further comprising programming the processor to request a reference measurement when it is determined that the level of the signal is below the predetermined threshold during the predefined period of time following sensor positioning.

5. The method of claim 1, wherein the predetermined threshold is related to a predefined signal attenuation level.

6. The method of claim 1, further comprising programming the processor not to report information related to the received glucose signal when it is determined that the level of the signal is below the predetermined threshold during the predefined period of time following sensor positioning.

7. The method of claim 1, wherein the glucose sensor comprises a plurality of electrodes including a working electrode, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

8. An in vivo glucose monitoring system, comprising:
    an in vivo glucose sensor configured for in vivo positioning such that at least a portion of the sensor is positioned in fluid contact with interstitial fluid; and
    a processor programmed to receive a signal from the in vivo glucose sensor, monitor the signal to determine if a level of the signal is below a predetermined threshold during a predefined period of time following sensor positioning, detect an attenuation in the signal when it is determined that the level of the signal is below the predetermined threshold during the predefined period of time following sensor positioning, categorize the detected attenuation in the signal based, at least in part, on one or more characteristics of the signal, and report information related to the signal when the level of the signal is not determined to be below the predetermined threshold during the predefined time period following sensor positioning, wherein the detected attenuation in the signal is associated with an early signal attenuation condition.

9. The system of claim 8, wherein the processor is programmed so that the predefined time period is within one day of sensor positioning.

10. The system of claim 9, wherein the processor is programmed so that the predefined time period is within one hour of sensor positioning.

11. The system of claim 8, wherein the processor is programmed to request a reference measurement when it is determined that the level of the signal is below the predetermined threshold during the predefined period of time following sensor positioning.

12. The system of claim 8, wherein the predetermined threshold is related to a predefined signal attenuation level.

13. The system of claim 8, wherein the processor is programmed to not report information related to the signal when it is determined that the level of the signal is below the predetermined threshold during the predefined period of time following sensor positioning.

14. The system of claim 8, wherein the in vivo glucose sensor comprises a plurality of electrodes including a working electrode, wherein the working electrode comprises a glucose-responsive enzyme and a mediator, wherein at least one of the glucose-responsive enzyme and the mediator is chemically bonded to a polymer disposed on the working electrode, and wherein at least one of the glucose-responsive enzyme and the mediator is crosslinked with the polymer.

15. An apparatus, comprising:
a processor programmed to receive a signal from a glucose sensor, monitor the signal to determine if a level of the signal is below a predetermined threshold during a predefined period of time following sensor positioning, detect an attenuation in the signal when it is determined that the level of the signal is below the predetermined threshold during the predefined period of time following sensor positioning, categorize the detected attenuation in the signal based, at least in part, on one or more characteristics of the signal, and report information related to the signal when the level of the signal is not determined to be below the predetermined threshold during the predefined time period following sensor positioning, wherein the detected attenuation in the signal is associated with an early signal attenuation condition.

16. The apparatus of claim 15, wherein the processor is programmed so that the predefined time period is within one day of sensor positioning.

17. The apparatus of claim 16, wherein the processor is programmed so that the predefined time period is within one hour of sensor positioning.

18. The apparatus of claim 15, wherein the processor is programmed to request a reference measurement when it is determined that the level of the signal is below the predetermined threshold during the predefined period of time following sensor positioning.

19. The apparatus of claim 15, wherein the predetermined threshold is related to a predefined signal attenuation level.

20. The apparatus of claim 15, wherein the processor is programmed to not report information related to the signal when it is determined that the level of the signal is below the predetermined threshold during the predefined period of time following sensor positioning.

* * * * *